United States Patent [19]

Kubota et al.

[11] Patent Number: 5,066,574

[45] Date of Patent: Nov. 19, 1991

[54] SILVER HALIDE PHOTOGRAPHIC LIGHT-SENSITIVE MATERIAL CONTAINING A NOVEL YELLOW COUPLER

[75] Inventors: Toru Kubota; Mayumi Tomotake; Hidenobu Ohya; Atsushi Tomotake; Noboru Mizukura, all of Hino, Japan

[73] Assignee: Konica Corporation, Tokyo, Japan

[21] Appl. No.: 591,293

[22] Filed: Oct. 1, 1990

[30] Foreign Application Priority Data

| | | | |
|---|---|---|---|
| Oct. 8, 1989 | [JP] | Japan | 1-262776 |
| Oct. 12, 1989 | [JP] | Japan | 1-266009 |
| Oct. 12, 1989 | [JP] | Japan | 1-266010 |

[51] Int. Cl.[5] ..... G03C 7/36

[52] U.S. Cl. ..... 430/557; 430/389; 430/556

[58] Field of Search ..... 430/557, 556, 389

[56] References Cited

U.S. PATENT DOCUMENTS

| | | | |
|---|---|---|---|
| 4,266,019 | 5/1981 | Kobayashi et al. | 430/557 |
| 4,269,936 | 5/1981 | Arai et al. | 430/557 |
| 4,404,274 | 9/1983 | Arai et al. | 430/557 |
| 4,791,050 | 12/1988 | Ogawa et al. | 430/557 |

FOREIGN PATENT DOCUMENTS

| | | |
|---|---|---|
| 267491 | 5/1988 | European Pat. Off. . |
| 2322615 | 11/1973 | Fed. Rep. of Germany . |

*Primary Examiner*—Richard L. Schilling
*Attorney, Agent, or Firm*—Jordan B. Bierman

[57] ABSTRACT

A silver halide photographic light-sensitive material which contains a noble 2-equivalent yellow coupler having an excellent color forming property and an improved dispersion stability in emulsion is disclosed. The coupler is represented by the following formula (I), (II), or (III):

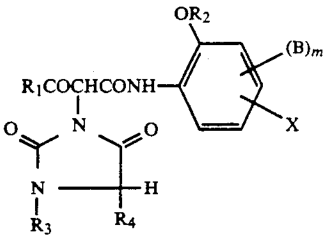

(I)

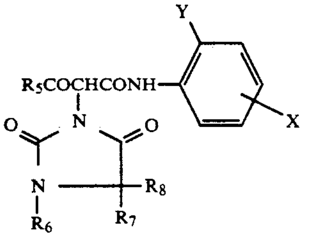

(II)

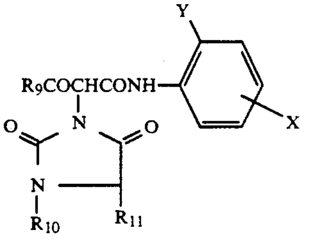

(III)

10 Claims, No Drawings

SILVER HALIDE PHOTOGRAPHIC LIGHT-SENSITIVE MATERIAL CONTAINING A NOVEL YELLOW COUPLER

FIELD OF THE INVENTION

The present invention relates to a silver halide photographic light-sensitive material, more particularly to a silver halide photographic light-sensitive material that uses a novel 2-equivalent yellow coupler having an excellent color forming property and causing less fog, and having an improved dispersing stability in emulsion as well.

BACKGROUND OF THE INVENTION

Yellow couplers are an essential component of a color photographic light-sensitive material, and 2-equivalent yellow couplers are used in the industry to obtain a maximum dye density and photographic sensitivity with a minimum amount of silver. As an coupling-off substituent in such 2-equivalent yellow couplers, there has been known an aryloxy group described in Japanese Patent Publication Open to Public Inspection (hereinafter referred to as Japanese Patent O.P.I. Publication) No. 87650/1975 and U.S. Pat. No. 3,408,194; an oxazolyloxy group described in Japanese Pat. O.P.I. Publication No. 131325/1976; a chroman-4-oxy group in the same Publication NO. 139333/1976; a tetrazolyloxy group in the same Publication No. 43426/1977; a 5-pyrazolyloxy group in the same Publication No. 150631/1977; a nitrogen-containing heterocyclic group in the same Publication No. 115219/1977; urazol group and hydantoin group in Japanese Pat. Examined Publication No. 33410/1976; and an arylthio group in U.S. Pat. No. 3,227,554.

On the other hand, requirements for coupler properties come to increasingly severe as the silver halide photographic light-sensitive material advances, and improvement in color forming efficiency is also required of the 2-equivalent yellow couplers. To meet with the requirement, there have been made various attempts in designing a coupler molecule, including proposals to introduce an alkoxycarbonyl group, or, a N-substituted or non-substituted alkylsulfonamide group or arylsulfonamide group as a ballast component. However, improvement in color forming property is not yet attained. A 2-equivalent yellow coupler with a hydantoin group as the coupling-off substituent is known to have an excellent color forming property, but it has disadvantage in poor solubility and unstable dispersibility in emulsion; therefore, improvement in these properties is strongly desired. Meanwhile, it is desired to reduce an amount of benzyl alcohol used in a color developer solution, or not to use it at all, in order to prevent environmental pollution and a problem caused by formation of tar in a developer solution. But, such reduction or nonuse of benzyl alcohol tends to lower the color forming property. Therefore, it is of much value to develop a yellow coupler which exhibits an excellent color forming property even in a developer solution containing little or no benzyl alcohol. But it cannot be said that study of the yellow coupler has been actively conducted with the view of solving the above problems.

SUMMARY OF THE INVENTION

The present invention has been achieved by taking notice of the above conditions. The primary object of the present invention is to provide a silver halide photographic light-sensitive material containing a novel 2-equivalent yellow coupler which causes less fog and exhibits an excellent color forming property even in a developer solution containing little or no benzyl alcohol.

The secondary object of the present invention is to provide a silver halide photographic light-sensitive material containing a novel 2-equivalent yellow coupler excellent in solubility and dispersion stability when incorporated in an emulsion.

The above objects of the invention have been attained, in a silver halide photographic light-sensitive material comprising a support bearing thereon at least one silver halide emulsion layer, by a silver halide photographic light-sensitive material in which at least one of said silver halide emulsion layers contains a coupler represented by the following Formulas (I), (II) or (III):

Formula (I)

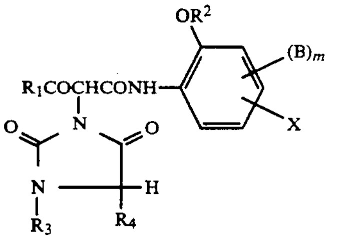

wherein $R_1$ and $R_2$ independently represent an alkyl group, cycloalkyl group or aryl group; $R_3$ and $R_4$ independently represent an alkyl group or cycloalkyl group; B represents a group capable of being substituted at a benzene ring; m represents an integer from 0 to 3; and X represents an acylamino group, sulfonamide group, oxycarbonyl group, carbamoyl group, sulfamoyl group, carbonyloxy group, oxycarbonylamino group, ureido group or sulfonyloxy group.

Formula (II)

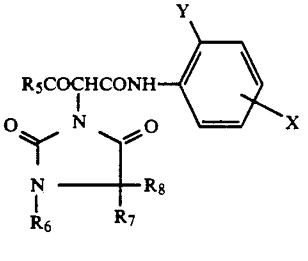

wherein $R_5$ represents an alkyl group or cycloalkyl group; $R_6$ and $R_7$ represent independently an alkyl group or cycloalkyl group, and $R_9$ represents a hydrogen atom, alkyl group or cycloalkyl group, provided that the total carbon number of $R_6$, $R_7$ and $R_8$ is 7 or less; X is the same as defined in Formula (I); and Y represents a halogen atom, amino group, alkylthio group or arylthio group.

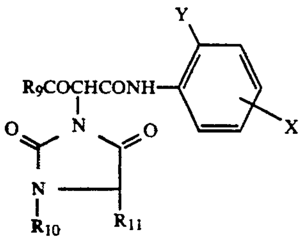

Formula (III)

wherein $R_9$ represents an aryl group; $R_{10}$ and $R_{11}$ independently represent an alkyl group or cycloalkyl group, provided that the total carbon number of the two is 9 or less; X and Y are the same as defined in Formulas (I) and (II).

DETAILED DESCRIPTION OF THE INVENTION

Examples of the alkyl group represented by $R_1$ in Formula (I) include linear or branched-chain alkyl groups such as methyl, ethyl, isopropyl, t-butyl and dodecyl groups.

Examples of the cycloalkyl group represented by $R_1$ include cyclopropyl, cyclohexyl and adamantyl groups. These alkyl and cycloalkyl groups represented by $R_1$ include ones having a substituent such as a halogen atom, aryl group, alkoxy group, aryloxy group, alkylsulfonyl group, acylamino group and hydroxy group. Of these groups, branched alkyl groups such as t-butyl group are preferable as $R_1$.

Examples of the aryl group represented by $R_1$ in Formula (I) include a phenyl group and p-(t-octyl)phenyl group. These aryl groups may have a substituent such as a halogen atom, alkyl group, aryl group, alkoxy group, aryloxy group, nitro group, cyano group and acylamino group.

Examples of the alkyl group, cycloalkyl and aryl group each represented by $R_2$ in Formura (I) include the same groups as specified in respect to $R_1$. These alkyl, cycloalkyl and aryl groups represented by $R_2$ may have the same substituent as specified in respect to $R_1$. Of them, linear or branched alkyl groups are preferred as $R_2$.

Examples of the alkyl group represented by $R_3$ in Formula (I) include linear or branched alkyl groups such as methyl, ethyl, n-propyl, isopropyl, n-butyl, t-butyl and dodecyl groups.

Examples of the cycloalkyl group represented by $R_3$ include cyclopropyl and cyclohexyl groups. These alkyl and cycloalkyl groups represented by $R_3$ include ones having a substituent such as a halogen atom, aryl group, alkoxy group, aryloxy group, hydroxy group, acyloxy group, acylamino group, carbamoyl group, alkylcarbamoyl group, alkyloxycarbamoyl group, aryloxycarbamoyl group, alkylsulfonyl group and arylsulfonyl group.

Examples of the alkyl group and cycloalkyl group each represented by $R_4$ include the same groups as $R_3$. The alkyl and cycloalkyl groups represented by $R_4$ include ones having the same substituent as specified in respect to $R_3$.

Examples of the group capable of being replaced at a benzene ring and represented by B in Formula (I) are a halogen atom, alkyl group, alkoxy group, aryloxy group, acyloxy group, acylamino group, carbamoyl group, alkylsulfonamide group, arylsulfonamide group, sulfamoyl group and imide group. m represents an integer from 0 to 3; B may be the same or different, provided that m is 2 or more.

Examples of the alkyl group represented by $R_5$ in Formula (II) include a methyl group, ethyl group, isopropyl group, t-butyl group and dodecyl group. These alkyl groups represented by $R_5$ may have a substituent such as a halogen atom, aryl group, alkoxy group, aryloxy group, alkyloxy group, acyloxy group and acylamino group.

Examples of the cycloalkyl group represented by $R_5$ include a cyclopropyl group, cyclohexyl group and adamantyl group.

$R_5$ is preferably a branched alkyl group. In Formula (II), X is the same as defined in Formula (I).

Examples of the alkyl group and cycloalkyl group each represented by $R_6$, $R_7$ or $R_8$ in Formula (II) are a methyl group, ethyl group, isopropyl group, hexyl group, cyclopentyl group and cyclohexyl group.

These alkyl and cycloalkyl groups each represented by $R_6$, $R_7$ or $R_8$ may have a substituent such as a halogen atom (e.g., chlorine atom or bromine atom), alkoxy group (e.g., methoxy, ethoxy or isopropoxy group), cycloalkyloxy group (e.g., cyclopentyloxy group), alkylthio group (e.g., methylthio group), alkylsulfonylamino group (e.g., methanesulfonylamino or n-buthanesulfonylamino group), alkylcarbonylamino group (e.g., acetylamino group), alkoxycarbonyl group (e.g., methoxycarbonyl or ethoxycarbonyl group) and heterocyclic group (e.g., terahydrofuryl, furyl or propanesaltonyl group).

Other than the above alkyl and cycloalkyl groups, $R_8$ represents a hydrogen atom.

$R_6$, $R_7$ and $R_8$ may be in any combination with one another, provided that each of which represents the above group; the total carbon number of $R_6$, $R_7$ and $R_8$ is 7 or less.

Examples of the halogen atom represented by Y in Formula (II) are a fluorine atom, chlorine atom, bromine atom and iodine atom.

The amino group represented by Y may be mono-substituted or di-substituted with groups such as alkyl, aryl, acyl and sulfonyl group; and examples of such amino group include a methylamino group, dimethylamino group, ethylamino group, isopropylamino group, dodecylamino group, phenylamino group, acetylamino group and benzylamino group.

Examples of the alkylthio group represented by Y are a methylthio group and arylthio group, and examples of the arylthio group represented by Y include a phenylthio group.

Y is preferably a halogen atom, particularly preferably a chlorine atom.

Examples of the aryl group represented by $R_9$ in Formula (III) include an aryl group having 6 to 30 carbon atoms such as a phenyl group. This aryl group may have a substituent such as a halogen atom, trifluoromethyl group, alkoxy group, aryloxy group, alkylcarbonyloxy group, arylcarbonyloxy group, alkylamino group, dialkylamino group, anilino group, alkylcarbonylamino group or arylcarbonylamino group. Of them, an alkoxy group is preferred, a methoxy group is particularly preferred.

Examples of the alkyl and cycloalkyl groups each represented by $R_{10}$ or $R_{11}$ in Formura (III) include a methyl group, ethyl group, isopropyl group, hexyl group, cyclopentyl group and cyclohexyl group.

These alkyl and cycloalkyl groups each represented by $R_{10}$ or $R_{11}$ may have a substituent such as a halogen atom (e.g., chlorine or bromine atom), alkoxy group (e.g., methoxy, ethoxy or isopropoxy group), cycloalkyloxy group (e.g., cyclopentyloxy group), alkylthio group (e.g., methylthio group), alkylsufonylamino group (e.g., methanesulfonamide or n-buthanesulfonylamide group), alkylcarbonylamino group (e.g., acetylamino group), alkoxycarbonyl group (e.g., methoxycarbonyl or ethoxycarbonyl group) and heterocyclic group (e.g., tetrahydrofuryl, furyl or propanesaltonyl group).

$R_{10}$ and $R_{11}$ may be in any combination, provided that they represent the above groups; and the total carbon number of the two is 9 or less.

In Formulas (I) (II) and (III), X represents an acylamino group, sulfonamide group, oxycarbonyl group, carbamoyl group, sufamoyl group, carbonyloxy group, oxycarbonylamino group, ureido group and sulfonyloxy group; and X is preferably selected from the following groups represented by Formuras (1) to (11).

$$-\underset{\displaystyle R_{13}}{N}SO_2R_{12}$$ Formula (1)

$$-CONR_{12}R_{13}$$ Formula (2)

$$-\underset{\displaystyle R_{13}}{N}COR_{12}$$ Formula (3)

$$-\underset{\displaystyle R_{13}}{N}CO-L-SO_2R_{12}$$ Formula (4)

$$-\underset{\displaystyle R_{13}}{N}CO\underset{\displaystyle R_{14}}{N}R_{12}$$ Formula (5)

$$-\underset{\displaystyle R_{13}}{N}COOR_{12}$$ Formula (6)

$$-OSO_2R_{12}$$ Formula (7)

$$-OCOR_{12}$$ Formula (8)

$$-COOR_{12}$$ Formula (9)

$$-COO-L-COOR_{12}$$ Formula (10)

-continued $$-SO_2\underset{\displaystyle R_{13}}{N}-R_{12}$$ Formula (11)

wherein $R_{12}$ represents an alkyl group, cycloalkyl group or aryl group; $R_{13}$ and $R_{14}$ independently represent a hydrogen atom or a group represented by $R_{12}$; and L represents a divalent organic linking group.

Examples of the alkyl and cycloalkyl groups each represented by $R_{12}$, $R_{13}$ or $R_{14}$ include a linear or branched alkyl and cycloalkyl groups (e.g., methyl, n-butyl, cyclohexyl, 2-ethylhexyl, n-dodecyl or n-hexadecyl group). Examples of the aryl group represented by $R_{12}$, $R_{13}$ or $R_{14}$ include an aryl group having 6 to 22 carbon atoms (e.g., phenyl or 1-naphthyl group).

These alkyl and cycloalkyl groups each represented by $R_{12}$, $R_{13}$ or $R_{14}$ may have a substituent such as a halogen atom (e.g., chlorin or bromine atom), aryl group (e.g., phenyl or 4-t-butylphenyl group), aryloxy group (e.g., phenoxy, p-methylphenoxy or 2,4-di-t-amylphenoxy group), alkoxy group (e.g., methoxy, ethoxy, i-propyloxy or n-dodecyloxy group), cycloalkyloxy (e..g, cyclohexyloxy group), alkylthio group (e.g., methylthio group), alkylsulfonylamino group (e.g., methanesulfonylamino or n-butanesulfonylamino group) and alkylcarbonylamino group (e.g., acetylamino or 3-(2,4-di-t-amylphenoxy)butanoylamino group).

The aryl group represented by $R_{12}$, $R_{13}$ or $R_{14}$ may have a substituent such as an alkyl group or the same group that can be introduced in the alkyl or cycloalkyl group represented by $R_{12}$, $R_{13}$ or $R_{14}$.

L in Formulas (4) and (10) represents a divalent organic linking group being a alkylene or arylene group. Examples of the alkylene group include linear or branched alkylene groups having 1 to 10 carbon atoms (e.g., methylene, ethylene, methylethylene, propylene, dimethylmethylene, butylene and hexylene groups). Examples of the arylene group represented by L include arylene groups having 6 to 14 carbon atoms (e.g., 1,2-phenylene, 1,4-phenylene and 1,4-naphthylene groups).

Each of the couplers represented by Formulas (I), (II) and (III) may link with one another via a polyvalent group to form a dimer, oligomer or much larger low polymer. In this case, the carbon number range defined for the forgoing substituents may not be applicable.

Typical examples of the 2-equivalent yellow couplers of the invention represented by Formulas (I), (II) and (III) are shown below, but the scope of the invention is not limited to these examples.

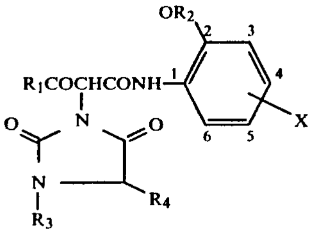
| No. | $R_1$ | $R_2$ | $R_3$ | $R_4$ | X (Substitutional position) |
|---|---|---|---|---|---|
| 1 | $-tC_4H_9$ | $-CH_3$ | $-C_4H_9$ | $-CH_3$ | $-NHSO_2C_{16}H_{33}$ (5) |
| 2 | $-tC_4H_9$ | $-CH_3$ | $-CH_2CH_2OCH_3$ | $-CH_3$ | $-NHSO_2C_{16}H_{33}$ (5) |
| 3 | $-tC_4H_9$ | $-CH_3$ | 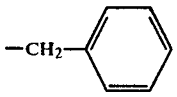 | $-CH_3$ | $-NHSO_2C_{16}H_{33}$ (5) |
| 4 | $-tC_4H_9$ | $-CH_3$ | $-C_4H_7$ | $-CH_3$ | 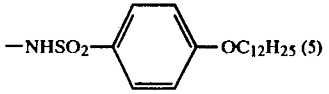 |
| 5 | $-tC_4H_9$ | $-C_{16}H_{33}$ | $-CH_3$ | $-CH_3$ | $-NHSO_2C_4H_9$ (5) |
| 6 | $-tC_4H_9$ | $-CH_3$ | $-CH_2CH_2(CH_3)_2$ | $-CH_3$ | 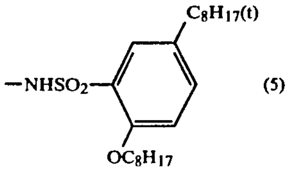 |
| 7 | $-tC_4H_9$ | $-CH_3$ | $-C_6H_{13}$ | $-CH_3$ | 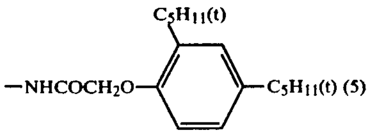 |
| 8 | $-tC_4H_9$ | $-CH_3$ | 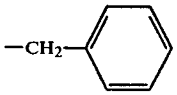 | $-CH_3$ | 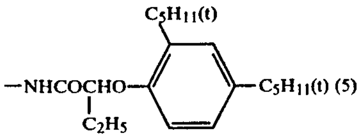 |

-continued
| | | | | | |
|---|---|---|---|---|---|
| 9 | $-tC_4H_9$ | 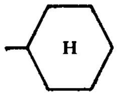 | $-CH_3$ | $-CH_3$ | 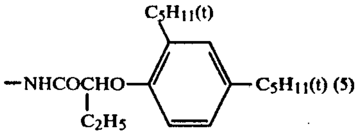 |
| 10 | $-tC_4H_9$ | $-CH_3$ | $-CH_2CH_2OH_3$ | $-CH_3$ | 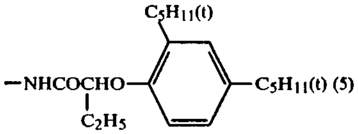 |
| 11 | $-tC_4H_9$ | $-CH_3$ | 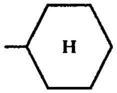 | $-CH_3$ | 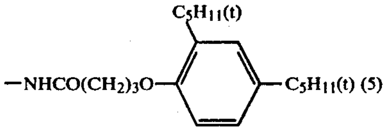 |
| 12 | $-tC_4H_9$ | $-CH_3$ | $-C_4H_9$ | $-CH_3$ | 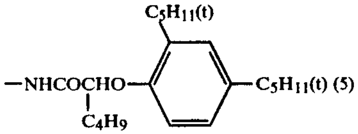 |
| 13 | $-tC_4H_9$ | $-CH_3$ | $-CH_3$ | $-CH_3$ | $-NHCOC_{11}H_{23}$ (5) |
| 14 | $-tC_4H_9$ | $-CH_3$ | $-CH_2CH_2OCH_3$ | $-CH_3$ | $-NHCOCHCH_2SO_2C_{12}H_{25}$ (5)<br>$CH_3$ |
| 15 | $-tC_4H_9$ | $-CH_3$ | $-CH_3$ | $-CH_3$ | $-NHCOCHCH_2SO_2C_{12}H_{25}$ (5)<br>$CH_3$ |
| 16 | $-tC_4H_9$ | $-CH_3$ | 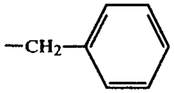 | $-CH_3$ | $-NHCOCHCH_2SO_2C_{12}H_{25}$ (5)<br>$CH_3$ |
| 17 | $-tC_4H_9$ | $-CH_3$ | $-C_4H_9$ | $-CH_3$ | $-NHCOCHCH_2SO_2C_{12}H_{25}$ (5)<br>$CH_3$ |

-continued

| | | | | | |
|---|---|---|---|---|---|
| 18 | $-tC_4H_9$ | $-CH_3$ | $-CH_2CH_2OC_2H_5$ | $-C_2H_5$ | $-NHCOCHCH_2SO_2C_{12}H_{25}$ (5)<br>$CH_3$ |
| 19 | $-tC_4H_9$ | $-CH_3$ | $-CH_2OH$ | $-CH_3$ | $-NHCOCHCH_2SO_2C_{12}H_{25}$ (5)<br>$CH_3$ |
| 20 | $-tC_4H_9$ | $-CH_3$ | $-CH_2CH_2OCH_2CH_2OC_4H_9$ | $-CH_3$ | $-NHCOCHCH_2SO_2C_{12}H_{25}$ (5)<br>$CH_3$ |
| 21 | $-tC_4H_9$ | 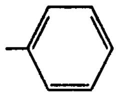 | $-CH_3$ | $-CH_3$ | $-NHCO(CH_2)_3SO_2C_{12}H_{25}$ (5) |
| 22 | $-tC_4H_9$ | $-CH_3$ | 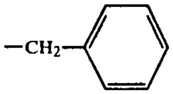 | $-CH_3$ | 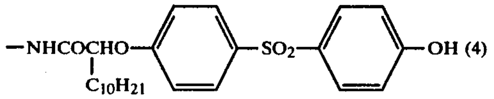 |
| 23 | $-tC_4H_9$ | $-CH_3$ | $-C_4H_9$ | $-CH_3$ | $-CO_2C_{12}H_{25}$ (5) |
| 24 | $-tC_4H_9$ | $-CH_3$ | $-C_4H_9$ | $-CH_3$ | $-CO_2CHCO_2C_{12}H_{25}$ (5)<br>$CH_3$ |
| 25 | $-tC_4H_9$ | $-CH_3$ | $-CH_2CH_2OC_2H_5$ | $-CH_3$ | $-CO_2CH_2CHC_8H_{17}$ (5)<br>$C_6H_{13}$ |
| 26 | $-tC_4H_9$ | $-CH_3$ | $-CH_3$ | $-CH_3$ | 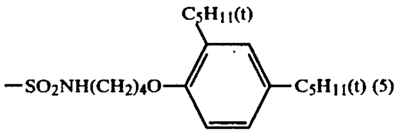 |
| 27 | $-tC_4H_9$ | $-CH_3$ | $-CH_3$ | $-CH_3$ | $-CONHC_{12}H_{25}$ (5) |
| 28 | $-tC_4H_9$ | $-C_2H_5$ | $-C_4H_9$ | $-CH_3$ | 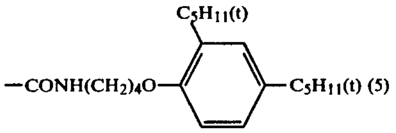 |
| 29 | $-tC_4H_9$ | $-CH_3$ | $-CH_3$ | $-CH_3$ | $-NHCOOC_{16}H_{33}$ (5) |

-continued
| | | | | | |
|---|---|---|---|---|---|
| 30 | 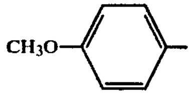 | $-CH_3$ | $-C_4H_9$ | $-CH_3$ | 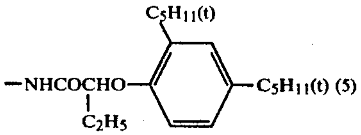 |
| 31 | 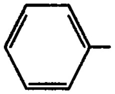 | $-CH_3$ | $-CH_3$ | $-CH_3$ | $-NHCO(CH_2)_3SO_2C_{12}H_{25}$ (5) |
| 32 | 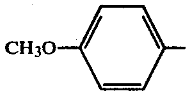 | $-CH_3$ | $-CH_3$ | $-CH_3$ | 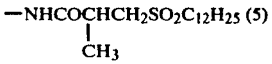 |
| 33 | 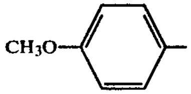 | $-CH_3$ | $-C_4H_9$ | $-CH_3$ | $-NHSO_2C_{16}H_{33}$ (5) |
| 34 | 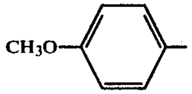 | $-CH_3$ | $-C_4H_9$ | $-CH_3$ | $-CO_2C_{12}H_{25}$ (5) |
| 35 | 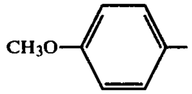 | $-CH_3$ | $-CH_3$ | $-CH_3$ | $-CO_2C_{12}H_{25}$ (5) |
| 36 | 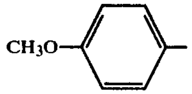 | $-CH_3$ | 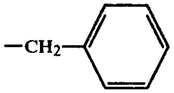 | $-CH_3$ | $-CO_2C_{12}H_{25}$ (5) |
| 37 | 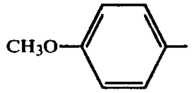 | $-CH_3$ | $-CH(CH_3)_2$ | $-CH_3$ | 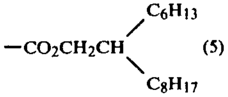 |

-continued
| | | | | | |
|---|---|---|---|---|---|
| 38 | 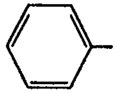 | $-CH_3$ | $-C_4H_9$ | $-CH_3$ | $-CO_2CHCO_2C_{12}H_{25}$ (5)<br>$CH_3$ |
| 39 | 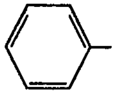 | $-CH_3$ | 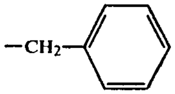 | $-CH_3$ | $-SO_2NHC_{16}H_{33}$ (5) |
| 40 | 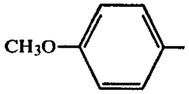 | $-CH_3$ | $CH_3$ | $-C_4H_9$ | $-CONHC_{12}H_{25}$ (5) |
| 41 | 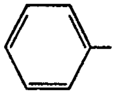 | $-CH_3$ | $-C_4H_9$ | $-CH_3$ | 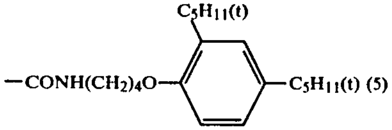 |
| 42 | 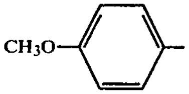 | $-CH_3$ | $-CH_2CH_2OC_2H_5$ | $-CH_3$ | $-OCOC_{11}H_{23}$ (5) |
| 43 | 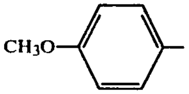 | $-CH_3$ | 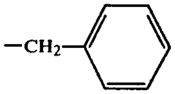 | $-CH_3$ | $-OCO_2C_{16}H_{33}$ (5) |
| 44 | 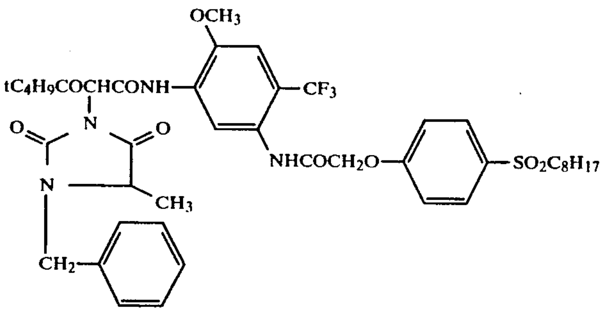 | | | | |

-continued
45
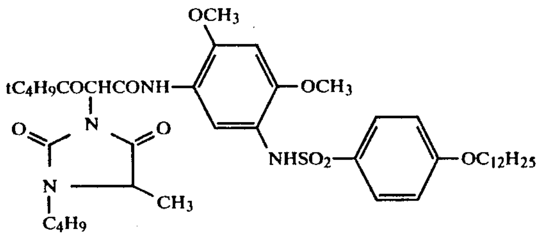
46
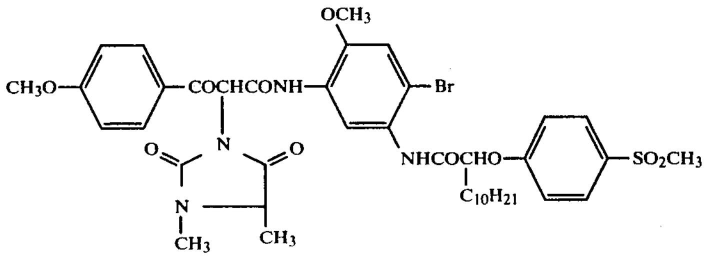
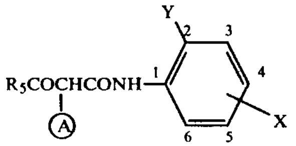
| No. | $R_5$ | Y | Ⓐ | X (Substitutional position) |
| --- | --- | --- | --- | --- |
| 47 | $(t)C_4H_9-$ | $-Cl$ | 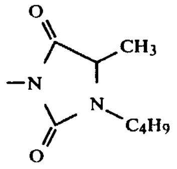 | 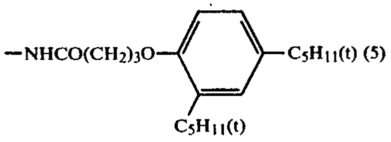 |
| 48 | $(t)C_4H_9-$ | 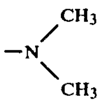 | 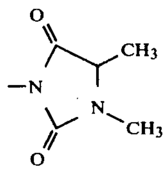 | 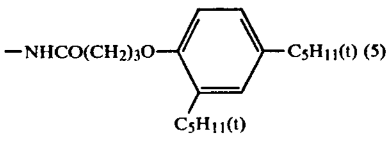 |

-continued
| | | | | |
|---|---|---|---|---|
| 49 | $(t)C_4H_9-$ | $-Cl$ | 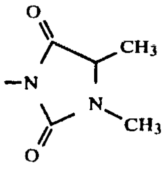 | $-NHCOCHCH_2SO_2C_{12}H_{25}$ (5)<br>$CH_3$ |
| 50 | $(t)C_4H_9-$ | $-Cl$ | 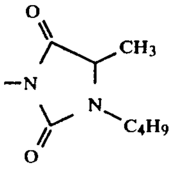 | $-NHCOCHCH_2SO_2C_{12}H_{25}$ (5)<br>$CH_3$ |
| 51 | $(t)C_4H_9-$ | $-Cl$ | 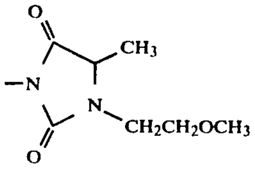 | $-NHCOCHCH_2SO_2C_{12}H_{25}$ (5)<br>$CH_3$ |
| 52 | $(t)C_4H_9-$ | $-SCH_3$ | 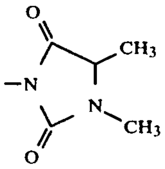 | $-NHCOCHCH_2SO_2C_{12}H_{25}$ (5)<br>$CH_3$ |
| 53 | $(t)C_4H_9-$ | $-Cl$ | 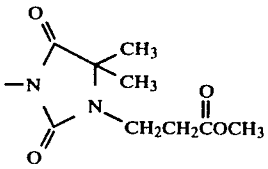 | $CH_3$<br>$-NHCOCCH_2SO_2C_{12}H_{25}$ (5)<br>$CH_3$ |
| 54 | $(t)C_4H_9-$ | $-Cl$ | 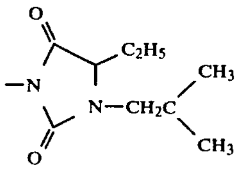 | $-NHCO(CH_2)_3SO_2C_{12}H_{25}$ (5) |

-continued
| | | | | |
|---|---|---|---|---|
| 55 | (t)$C_4H_9$— | —F | 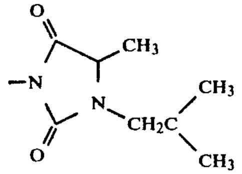 | $—NHCO(CH_2)_3SO_2C_{10}H_{21}$ (5) |
| 56 | (t)$C_4H_9$— | $—NHSO_2CH_3$ | 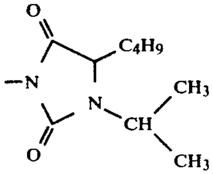 | $—CONHC_{12}H_{25}$ (5) |
| 57 | (t)$C_4H_9$— | —Cl | 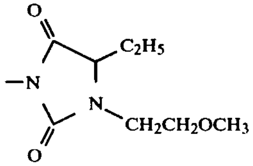 | 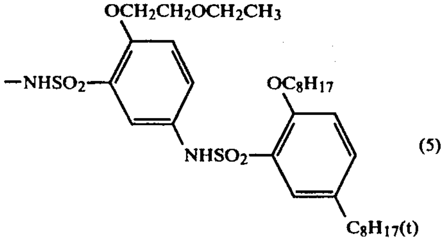 (5) |
| 58 | (t)$C_4H_9$— | —Cl | 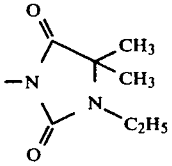 | $—COOC_{12}H_{25}$ (5) |
| 59 | (t)$C_4H_9$— | —Cl | 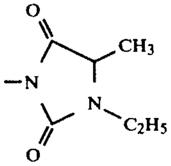 | $—COOCHCOOC_{12}H_{25}$ (5) with $CH_3$ on the CH |

-continued
| | | | | |
|---|---|---|---|---|
| 60 | (t)$C_4H_9$— | —Cl | 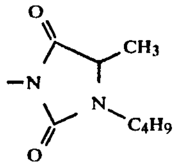 | —$NHSO_2C_{16}H_{33}$ (5) |
| 61 | (t)$C_4H_9$— | —Cl | 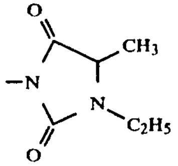 | 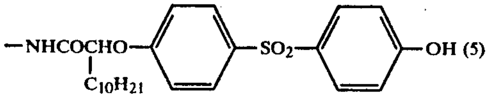 |
| 62 | (t)$C_4H_9$— | —Cl | 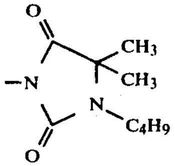 | —$NHCOOC_{16}H_{33}$ (5) |
| 63 | (t)$C_4H_9$— | —Cl | 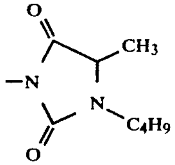 | 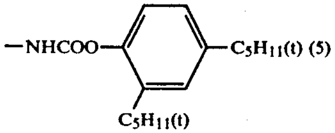 |
| 64 | (t)$C_4H_9$— | —Cl | 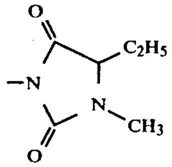 | 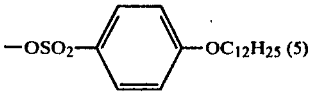 |
| 65 | (t)$C_4H_9$— | —Cl | 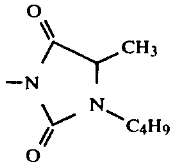 | —$OCOC_{11}H_{23}$ (5) |

-continued
| | | | | |
|---|---|---|---|---|
| 66 | (t)$C_4H_9$— | —Cl | 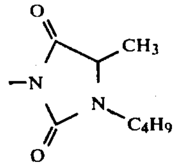 | 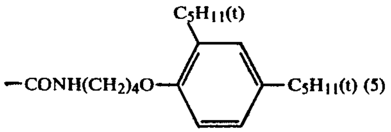 |
| 67 | (t)$C_4H_9$— | —Cl | 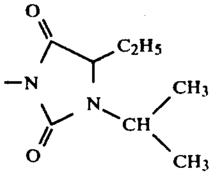 | 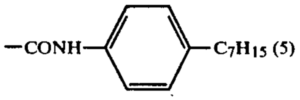 |
| 68 | (t)$C_4H_9$— | —Cl | 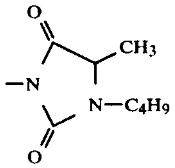 | $-CONHC_{12}H_{25}$ (5) |
| 69 | (t)$C_4H_9$— | —Cl | 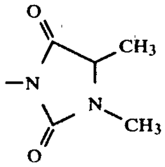 | $-NHCONHC_{12}H_{25}$ (5) |
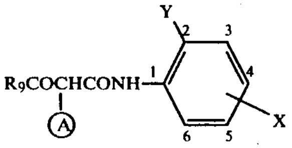
| No. | $R_9$ | Y | Ⓐ | X (Substitutional position) |
|---|---|---|---|---|
| 70 | 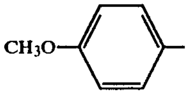 | —Cl | 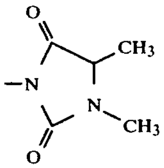 | $-NHSO_2C_{16}H_{33}$ (5) |

-continued
| | | | | |
|---|---|---|---|---|
| 71 | 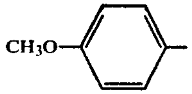 | —Cl | 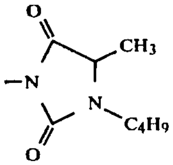 | $-NHSO_2C_{16}H_{33}$ (5) |
| 72 | 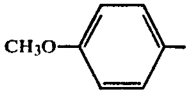 | —Cl | 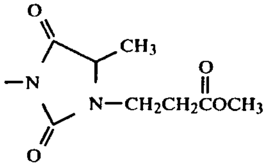 | $-NHSO_2C_{16}H_{33}$ (5) |
| 73 | 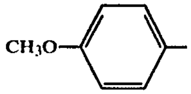 | —Cl | 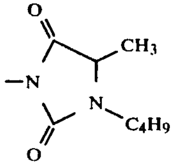 | 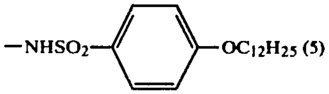 |
| 75 | 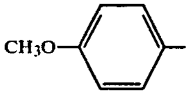 | —F | 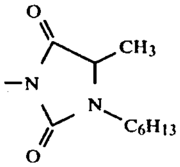 | 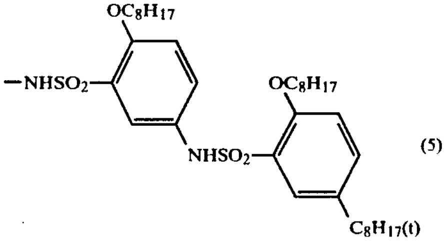 |
| 76 | 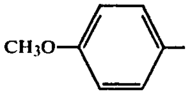 | —Cl | 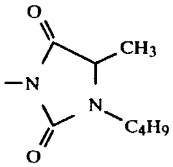 | $-COOC_8H_{17}$ (5) |

-continued
| | | | | |
|---|---|---|---|---|
| 77 | 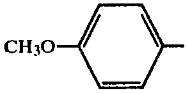 | —Cl | 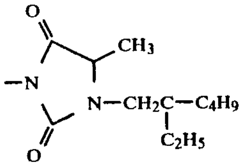 | $-COOC_8H_{17}$ (5) |
| 78 | 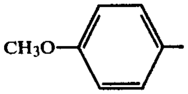 | —Cl | 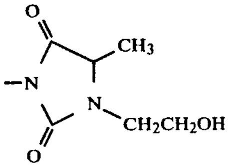 | $-NHSO_2C_{12}H_{25}$ (5) |
| 79 | 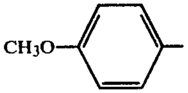 | —Cl | 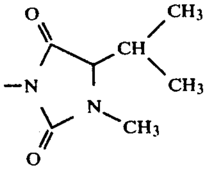 | 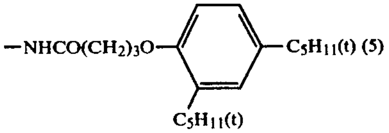 |
| 80 | 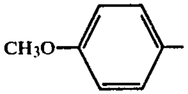 | —Cl | 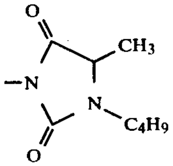 | $-NHCOCHCH_2SO_2C_{12}H_{25}$ (5)<br>$CH_3$ |
| 81 | 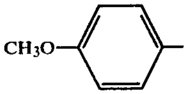 | —Cl | 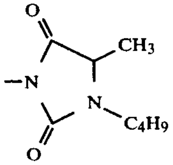 | 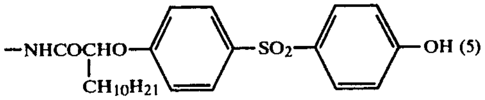 |
| 82 | 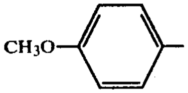 | —Cl | 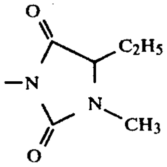 | $-NHCOOC_{16}H_{33}$ (5) |

-continued
| | | | | |
|---|---|---|---|---|
| 83 | 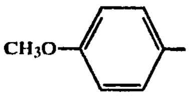 | —Cl | 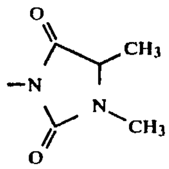 | $-CONHC_{12}H_{25}$ (5) |
| 84 | 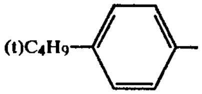 | —Cl | 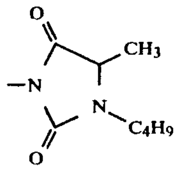 | $-CONHC_{12}H_{25}$ (5) |
| 85 | 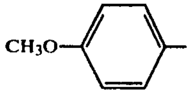 | —Cl | 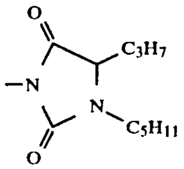 | 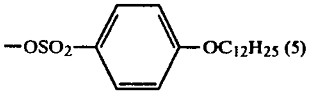 |
| 86 | 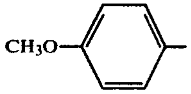 | —Cl | 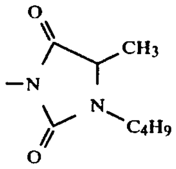 | $-OCOC_{11}H_{23}$ (5) |
| 87 | 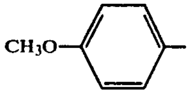 | —Cl | 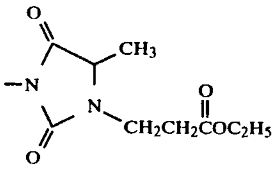 | $-OSO_2C_{16}H_{33}$ (5) |
| 88 | 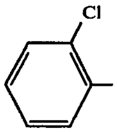 | —F | 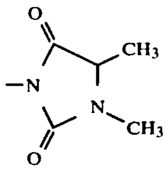 | $-OCOC_{16}H_{33}$ (5) |

-continued
| | | | | |
|---|---|---|---|---|
| 89 | 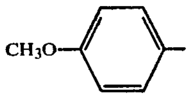 | —Cl | 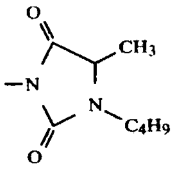 | $-NHCONHC_{12}H_{25}$ (5) |
| 90 | 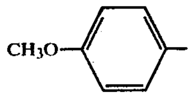 | —Cl | 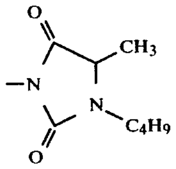 | 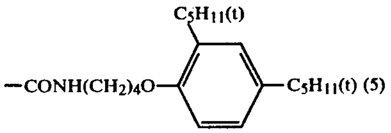 |
| 91 | 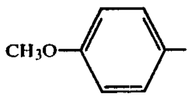 | —Cl | 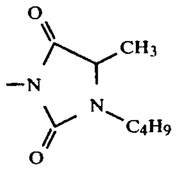 | 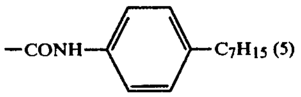 |

The yellow couplers of the invention can be synthesized by known methods. The following are examples of typical methods for synthesizing couplers of the invention.

Synthesis 1 (synthesis of Example Coupler 15)

A solution of 12.8 g of -chloro- -pivaloyl-2-methoxy-5-( -methyl- -dodecylsulfonylpropanoylamino) acetanilide, 3.3 g of 1,5-dimethylhydantoin and 3.8 g of potassium carbonate in 100 ml of acetone was refluxed for 6 hours upon continued heating. Then, acetone was removed by vacuum distillation. The residue was dissolved in 200 ml of ethylacetate and washed three times with 100 ml of 3-N hydrochloric acid. The organic layer was then separated and dried with magnesium sulfate. After filtering off the insoluble matter, the solvent was removed by vacuum distillation. The product was purified by column chromatography to obtain 9.1 g of Example Coupler 15. The yield was 62%.

Synthesis 2 (synthesis of Example Coupler 35)

A solution of 10.4 g of -chloro- -(4-methoxybenzoyl)-2-methoxy-5-dodecyloxycarbonylacetanilide and 6.4 g of potassium 1,5-dimethylhydantoin in 150 ml of acetone was refluxed for 8 hours upon continued heating. Then, after-treatments were carried out in the same procedure as in Synthesis 1. Purification by column chromatography gave 6.7 g (yield: 55%) of Example Coupler 35.

The structures of Example Couplers 15 and 35 were identified by NMR spectrums, IR spectrums and mass spectrums.

Synthesis 3 (synthesis of Example Coupler 49)

There was added 6.6 g of potassium carbonate to 100 ml of acetone solution containing 25.1 g of α-chloro-α-pivaloyl-2-chloro-5-(α-methyl-β-dodecylsulfonylpropanoylamino)acetanilide and 6.1 g of 1,5-dimethyl-2,4-dioxoimidazoline, and the mixture was refluxed for 3 hours upon heating. After filtering off the insoluble matter, acotone was distilled out from the filtrate, and then ethyl acetate was added thereto. The solution was washed with an aqueous solution of potassium carbonate, followed by washing with water and neutralizing with a dilute hydrochloric acid. After drying with magnesium sulfate, ethylacetate was removed by vacuum distillation. The residue was recrystallized from 100 ml of methanol to obtain the objective compound. The yield was 20.8 g (72%). The structure was identified by means of NMR, IR and mass spectrums.

Synthesis 4 (synthesis of Example Coupler 70)

A solution of 10 g of α-bromo-α-(4methoxybenzoyl)-2-chloro-5-hexadecanylsulfonylaminoacetanilide, 4.8 g of potassium 1,5,5-trimethyl-2,4-dioxoimidazolidine and 50 ml of DMF was heated at 60° C. for 3 hours. After completion f the reaction, 100 ml of water was added thereto, then ethyl acetate was added for extraction. The organic portion was washed with an aqueous solution of potassium carbonate, rinsed with water and neutralized with a dilute hydrochloric acid. After drying the solution with magnesium sulfate, ethyl acetate was removed by vacuum distillation, and the resulting residue was recrystallized from 50 ml of methanol to obtain the objective compound. The yield was 7.26 g (68%). The structure was identified by NMR, IR and mass spectrums.

The other couplers of the invention were synthesized from corresponding raw materials by the same procedures as in Synthesises 1 to 4.

The yellow couplers of the invention may be used singly or in combination of two or more. Further, they may be used together with a noninventive yellow coupler of pivaloylacetanilide type or benzoylacetanilide type.

In incorporating the yellow couplers of the invention in a silver halide photographic emulsion, the couplers are first dissolved singly or in combination in a high boiling organic solvent such as tricresyl phosphate or dibutyl phthalate, each which has a boiling point above 175° C., or in a low boiling organic solvent such as ethyl acetate or butyl propionate, or a mixture thereof. The solution is mixed with an aqueous solution of gelatin containing a surfactant and then dispersed with a high-speed rotary mixer or colloid mill. The dispersion is directly added to a silver halide photographic emulsion, then the emulsion is coated on a support and dried; or the dispersion is allowed to set and divided into portions, after removing the low boiling organic solvent by means such as washing, it is added to an emulsion to be coated and dried on a support.

In general, the yellow couplers of the invention are preferably used in an amount of 10 to 300 g per mol of silver halide, but the addition amount may vary according to specific requirements.

The silver halide photographic light-sensitive material of the invention may be of any kind and for any use. Silver halides usable in the invention are silver chloride, silver bromide, silver iodide, silver bromochloride, silver bromoiodide and silver bromochloroiodide.

The silver halide photographic light-sensitive material may contain color couplers other than the yellow couplers of the invention in order to form multicolor images.

In the silver halide photographic light-sensitive material of the invention, there may be arbitrarily contained a variety additives such as an antistain agent, image stabilizer, hardener, plasticizer, polymer latex, formalin scavenger, mordant, development accelerator, development retarder, fluorescent whitening agent, matting agent, solvent, antistatic agent and surfactant.

In addition, the silver halide photographic light-sensitive material comprising the yellow coupler of the invention may contain an ultra violet absorbent so that stability of yellow images can be further improved.

EXAMPLES

The present invention is hereunder described in more detail with examples, but the embodiments of the invention are not limited to these examples.

EXAMPLE 1

10.0 g each of the yellow couplers of the invention shown in Table 1 (denoted by the number given to each example coupler) and the comparative couplers represented by Y-1 to Y-4 was dissolved at 50° C. in a mixture of 2.0 ml of dibutyl phthalate and 20 ml of ethyl acetate. The solution thus prepared was mixed with 5 ml of 10% aqueous solution of Alkanol B (alkylnaphthalene sulfonate made by Du pont) and 100 ml of 5% aqueous gelatin, the mixture was then emulsified by being passed through a colloid mill several times to prepare an emulsion for each of the foregoing couplers. Thus, Samples 1 to 8 of the invention and Comparative Samples 1 to 4 were obtained.

These emulsion samples were stored for 48 hours at 20° C., then the condition of each coupler was visually observed through a 20-power magnifier. The results are shown in Table 1.

TABLE 1

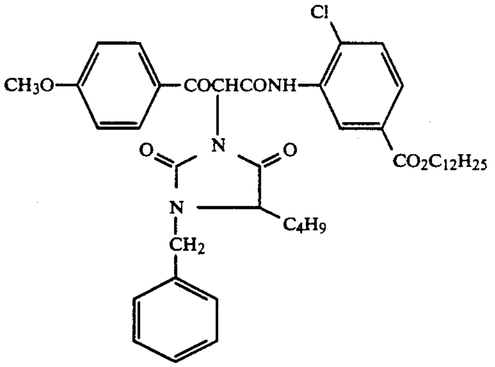

Y-1

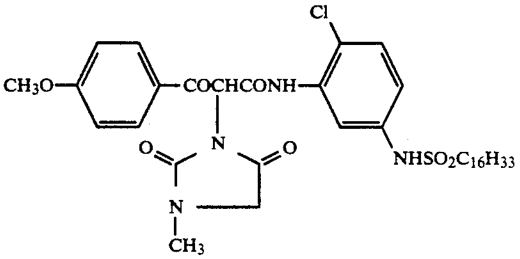

Y-2

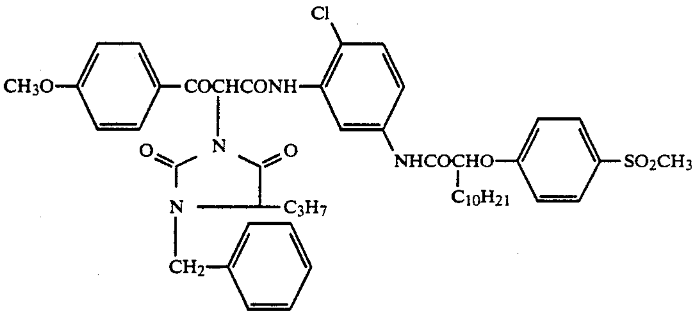

Y-3

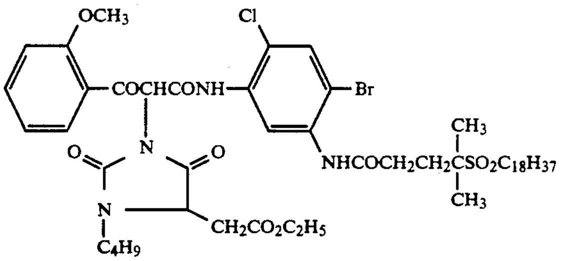

Y-4

| Sample No. | | Coupler | | Coupler condition after storage |
|---|---|---|---|---|
| Sample of the invention | 1 | Example Coupler | 70 | No precipitation |
| | 2 | | 71 | No precipitation |
| | 3 | | 72 | No precipitation |
| | 4 | | 73 | No precipitation |
| | 6 | | 75 | No precipitation |
| | 7 | | 76 | No precipitation |
| | 8 | | 78 | No precipitation |
| Comparative Sample | 1 | Comparative coupler | Y-1 | Slight precipitation |
| | 2 | | Y-2 | Slight precipitation |
| | 3 | | Y-3 | Heavy precipitation |
| | 4 | | Y-4 | Heavy precipitation |

It is understood from the results shown in Table 1 that Samples 1 to 8 of the invention do not cause precipitation of couplers; that is, the couplers of the invention are excellent in dispersion stability when stored in an emulsion state.

EXAMPLE 2

$3.0\times10^{-}$ mols each of the yellow couplers of the invention shown in Table 2 (denoted by the number given to each example coupler) and the comparative couplers represented by Y-5 and Y-6 was dissolved at 50° C. in a mixture of dibutyl phthalate in an amount corresponding to ¼ the weight of each yellow coupler and 40 ml of ethyl acetate . The solution was mixed with 10 ml of 10% aqueous solution of Alkanol B and 200 ml of 5% aqueous gelatin, the mixtures was then emulsified by being passed through a colloid mill several times. Twelve kinds of dispersion (A) containing respective couplers were thus prepared, and their turbidities were measured with a integrating sphere type turbidimeter made by Nippon Seimitsu Kogaku, Ltd. Then, each ½ the volume of the dispersion (A) was stored at 40° C. for 8 hours to obtain dispersion (B), turbidities of these dispersions were measured in the same manner as in Example 1. The results of the measurements are shown in Table 2.

Next, the dispersions (A) and (B) were each added to 500 ml of silver chlorobromide emulsion, then each of the emulsions so prepared was coated on a polyethylene laminated paper to a coating weight of 0.25 g $AgX/m^2$ and dried to obtain Samples 9 to 16 consisting of silver halide color photographic light-sensitive materials of the invention and Comparative Samples 5 and 6.

Each sample was exposed through an optical wedge in a normal manner and processed according to the following developing procedure and recipes of processing solutions.

| [Processing] | Temperature | Time |
|---|---|---|
| Color developing | 38° C. | 3 min 30 sec |
| Bleach-fixing | 33° C. | 1 min 30 sec |
| Washing | 33° C. | 3 min |

-continued

| | | |
|---|---|---|
| Drying | 50 to 80° C. | 2 min |

[Composition of color developer]

| | |
|---|---|
| Benzyl alcohol | 12 ml |
| Diethylene glycol | 10 ml |
| Potassium carbonate | 25 g |
| Sodium bromide | 0.6 g |
| Anhydrous sodium sulfite | 2.0 g |
| Hydroxylamine sulfate | 2.5 g |
| N-ethyl-N-β-methanesulfonamidoethyl-3-methyl-aminoaniline sulfate | 4.5 g |
| Water was added to make 1 l, then pH was adjusted to 10.2 with NaOH. | |

[Composition of bleach-fixer]

| | |
|---|---|
| Ammonium thiosulfate | 120 g |
| Sodium metabisulfite | 15 g |
| Anhydrous sodium sulfite | 3 g |
| Ammonium ferric EDTA | 65 g |
| Water was added to make 1 l, then pH was adjusted to 6.7 to 6.8. | |

The maximum color density of dye images formed on each sample through the above processes was measured together with the sensitivity of each sample. The results are shown in Table 2.

Y-5

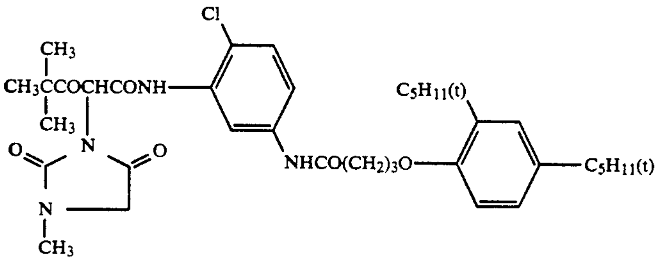

(a coupler described in Japanese Patent Examined Publication No. 10783/1976)

Y-6

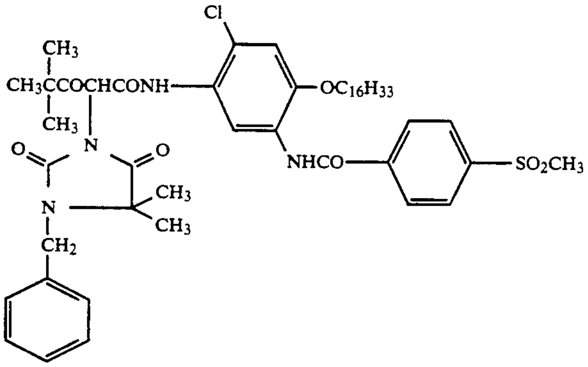

(a coupler described in Japanese Patent O.P.I. Publication No. 240060/1986

TABLE 2

| Sample No. | Coupler | Turbidity (ppm) Dispersion (A) | Turbidity (ppm) Dispersion (B) | Samples using Dispersion (A) Sensitivity | Samples using Dispersion (A) Maximum turbidity | Samples using Dispersion (B) Sensitivity | Samples using Dispersion (B) Maximum turbidity |
|---|---|---|---|---|---|---|---|
| Sample of the Invention | Example coupler | | | | | | |
| 9 | 47 | 22 | 31 | 118 | 2.47 | 110 | 2.24 |
| 10 | 49 | 13 | 25 | 131 | 2.62 | 122 | 2.37 |
| 11 | 51 | 17 | 30 | 127 | 2.58 | 119 | 2.33 |
| 12 | 54 | 19 | 27 | 120 | 2.57 | 109 | 2.25 |
| 13 | 55 | 11 | 22 | 122 | 2.52 | 113 | 2.29 |
| 14 | 57 | 25 | 45 | 128 | 2.55 | 121 | 2.27 |
| 15 | 59 | 20 | 36 | 130 | 2.60 | 121 | 2.38 |
| 16 | 65 | 15 | 33 | 117 | 2.46 | 106 | 2.22 |
| Comparative Sample | Comparative coupler | | | | | | |

TABLE 2-continued

| | | Turbidity (ppm) | | Samples using Dispersion (A) | | Samples using Dispersion (B) | |
|---|---|---|---|---|---|---|---|
| Sample No. | Coupler | Dispersion (A) | Dispersion (B) | Sensitivity | Maximum turbidity | Sensitivity | Maximum turbidity |
| 5 | Y-5 | 42 | 100 | 100 | 2.02 | 78 | 1.65 |
| 6 | Y-6 | 35 | 91 | 105 | 1.98 | 55 | 1.58 |

*The sensitivity is expressed by the value relative to that of Comparative Sample 1 which is set at 100.

It can be seen in Table 2 that the samples of the invention yield higher maximum color densities than the comparative samples in both dispersions (A) and (B), and cause less deterioration in sensitivity and maximum color density in samples that use dispersion (B). This means that the couplers of the invention have an excellent dispersion stability not only right after the preparation of dispersion but also after the storage of dispersion.

EXAMPLE 3

Dispersions (A) and (B) were prepared in the same manner as in Example 2 using the yellow couplers of the invention shown in Table 3 (denoted by the number given to each example coupler) and the following comparative couplers Y-7 to Y-10, and then their turbidities were measured.

Each of these dispersions was added to an silver chlorobromide emulsion; the emulsion was then coated on a polyethylene laminated paper, and dried to prepare samples.

Comparative coupler

Y-7

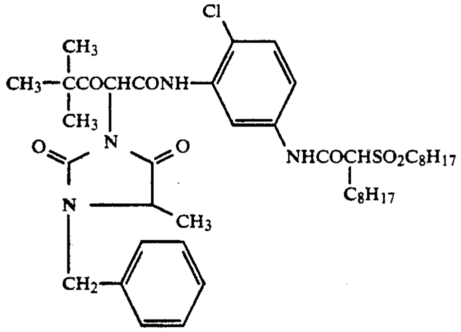

(a coupler described in Japanese Patent O.P.I. Publication No. 70841/1980)

Y-8

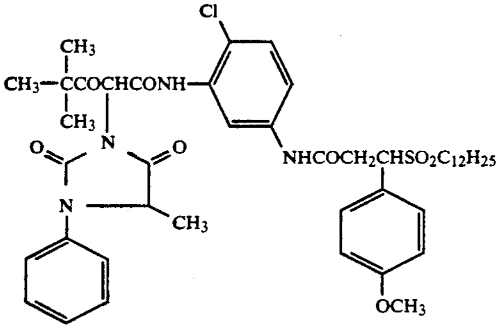

(a coupler described in Japanese Patent O.P.I. Publication No. 70841/1980)

-continued

Comparative coupler

Y-9

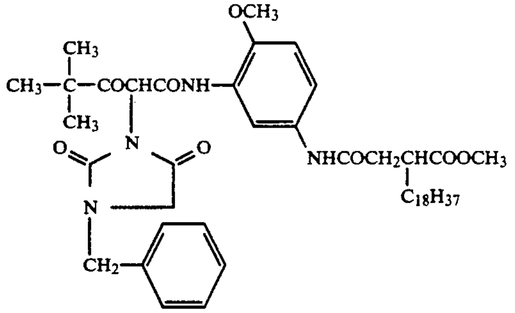

(a coupler described in Japanese Patent O.P.I. Publication No. 123047/1988)

Y-10

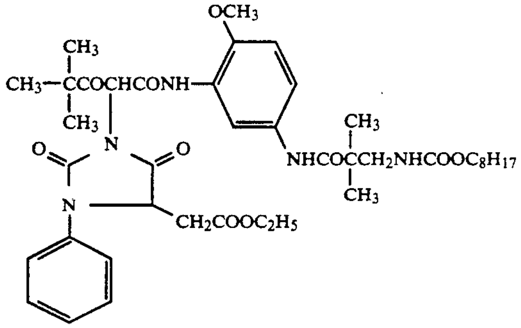

(a coupler described in Japanese Patent O.P.I. Publication No. 123047/1988)

The samples prepared as above were exposed through an optical wedge and processed according to the following developing procedure and recipes of processing solutions.

| Processing step | Temperature | Time |
|---|---|---|
| Color developing | 38° C. | 3 min 30 sec |
| Bleach-fixing | 38° C. | 1 min 30 sec |
| Washing | 38° C. | 2 min 0 sec |
| Stabilizing | 38° C. | 1 min 0 sec |

[Composition of color developer A]

| | |
|---|---|
| Benzyl alcohol | 15 ml |
| Sodium hexametaphosphate | 3.00 g |
| Anhydrous sodium sulfite | 1.85 g |
| Sodium bromide | 1.40 g |
| Potassium bromide | 0.50 g |
| Borax ($Na_2B_4O_7$ E10$H_2O$) | 39.10 g |
| N-ethyl-N-[2-(methanesulfonamidoethyl)-3-methyl-4-aminoaniline sulfate | 4.5 g |

Water was added to make 1 l, then pH was adjusted to 10.3 with NaOH.

[Composition of bleach-fixer]

| | |
|---|---|
| Ammonium ferric EDTA | 61.0 g |
| Diammonium EDTA | 5.0 g |
| Ammonium thiosulfate | 124.5 g |
| Sodium metabisulfite | 13.3 g |
| Sodium bisulfite | 2.7 g |

Water was added to 1 l, then pH was adjusted to 6.5.

[Composition of stabilizer]

-continued

| | |
|---|---|
| Glacial acetic acid | 20 ml |

800 ml of water was added, and pH was adjusted to 3.5 to 4.0 with sodium acatate trihydrate, then the total volume was made up to 1l.

Color developer B was prepared with the same composition as in Color developer A, except that the amount of benzyl alcohol was decreased to 1.0 ml.

The turbidities of the dispersions and the evaluation results of dye images formed by color developing are shown in Table 3.

TABLE 3

| | | Turbidity (ppm) | | Developer (A) Dispersion (A) | | | |
|---|---|---|---|---|---|---|---|
| Sample No. | Coupler | Dispersion (A) | Dispersion (B) | Fog | Sensitivity | Maximum density | Fog |
| 17(Invention) | 1 | 28 | 32 | 0.02 | 100 | 2.53 | 0.03 |
| 18(Invention) | 4 | 26 | 29 | 0.02 | 103 | 2.55 | 0.03 |
| 19(Invention) | 10 | 30 | 33 | 0.03 | 101 | 2.52 | 0.03 |
| 20(Invention) | 15 | 20 | 22 | 0.02 | 105 | 2.61 | 0.02 |
| 21(Invention) | 17 | 24 | 25 | 0.02 | 104 | 2.58 | 0.03 |
| 22(Invention) | 23 | 31 | 35 | 0.03 | 102 | 2.56 | 0.03 |
| 23(Invention) | 24 | 33 | 35 | 0.03 | 101 | 2.51 | 0.02 |
| 24(Invention) | 25 | 28 | 31 | 0.02 | 104 | 2.58 | 0.03 |
| 25(Invention) | 28 | 36 | 39 | 0.04 | 101 | 2.54 | 0.02 |
| 26(Invention) | 32 | 29 | 33 | 0.02 | 101 | 2.51 | 0.03 |
| 7(Comparison) | Y-7 | 50 | 132 | 0.02 | 80 | 2.17 | 0.03 |
| 8(Comparison) | Y-8 | 65 | 129 | 0.03 | 69 | 1.90 | 0.03 |
| 9(Comparison) | Y-9 | 63 | 180 | 0.03 | 59 | 1.73 | 0.03 |
| 10(Comparison) | Y-10 | 48 | 125 | 0.04 | 78 | 1.84 | 0.04 |

| | Developer (A) Dispersion (B) | | | Developer (B) Dispersion (B) | |
|---|---|---|---|---|---|
| Sample No. | Sensitivity* | Maximum density | Fog | Sensitivity | Maximum density |
| 17(Invention) | 100 | 2.48 | 0.03 | 96 | 2.28 |
| 18(Invention) | 103 | 2.54 | 0.02 | 94 | 2.31 |
| 19(Invention) | 100 | 2.50 | 0.03 | 94 | 2.30 |
| 20(Invention) | 104 | 2.59 | 0.03 | 98 | 2.35 |
| 21(Invention) | 103 | 2.57 | 0.03 | 97 | 2.33 |
| 22(Invention) | 101 | 2.51 | 0.02 | 96 | 2.24 |
| 23(Invention) | 101 | 2.49 | 0.02 | 95 | 2.29 |
| 24(Invention) | 102 | 2.56 | 0.02 | 95 | 2.29 |
| 25(Invention) | 101 | 2.51 | 0.03 | 98 | 2.28 |
| 26(Invention) | 100 | 2.46 | 0.03 | 96 | 2.21 |
| 7(Comparison) | 70 | 1.72 | 0.03 | 51 | 1.38 |
| 8(Comparison) | 68 | 1.69 | 0.02 | 53 | 1.31 |
| 9(Comparison) | 52 | 1.50 | 0.02 | 50 | 1.30 |
| 10(Comparison) | 71 | 1.77 | 0.02 | 64 | 1.44 |

*The sensitivity is expressed by a value relative to those of Sample 1 in Dispersion (A) and Dispersion (B) of Developer (A) which are set at 100 respectively.

As apparent from Table 3, Comparative Samples 7 to 10 are inferior in dispersion stability on storing and poor in sensitivity and maximum density when developed in Developer (A) containing benzyl alcohol. Moreover, when they were developed with Developer (B) containing less benzyl alcohol, a sensitivity drop and a noticeable deterioration in maximum density were observed.

Contrary to the above, Samples 17 to 26 using the yellow couplers of the invention are good in dispersion stability and capable of providing a higher sensitivity and maximum density without causing a substantial lowering in maximum density when Developer (A) is used. Further, these samples exhibit a better color forming property and a less tendency to lower the maximum density than the comparative samples even when processed in Developer (B) containing a reduced amount of benzyl alcohol.

EXAMPLE 4

On a paper support laminated with polyethylene on both sides were coated in sequence the layers having the following compositions respectively in order to prepare Sample 27 of a multicolor silver halide photographic light-sensitive material of the invention.

| | |
|---|---|
| 1st layer: blue-sensitive silver halide emulsion layer | |
| Monodispersed silver bromochloride emulsion containing 99.5 mol % or more of AgCl | 3.2 mg/100 $cm^2$ (in terms of silver) |
| Example Compound 1 | 6.7 mg/100 $cm^2$ |
| Dibutyl phthalate | 3.5 mg/100 $cm^2$ |
| Gelatin | 13.5 mg/100 $cm^2$ |
| 2nd layer: intermediate layer | |
| A gelatin layer containing HQ-1 | 0.5 mg/100 $cm^2$ |
| Dibutyl phthalate | 0.5 mg/100 $cm^2$ |
| Gelatin | 9.0 mg/100 $cm^2$ |
| 3rd layer: green-sensitive silver halide emulsion layer | |
| Monodispersed silver bromochloride emulsion containing 99.5 mol % or more of AgCl | 2.5 mg/100 $cm^2$ (in terms of silver) |
| Magenta coupler (M-1) | 3.5 mg/100 $cm^2$ |
| Dibutyl phthalate | 3.0 mg/100 $cm^2$ |
| Gelatin | 12.0 mg/100 $cm^2$ |
| 4th layer: intermediate layer | |
| A gelatin layer containing UV-absorbent (UV-1) | 0.7 mg/100 $cm^2$ |
| Dibutyl phthalate | 6.0 mg/100 $cm^2$ |
| HQ-1 | 0.5 mg/100 $cm^2$ |
| Gelatin | 12.0 mg/100 $cm^2$ |
| 5th layer: red-sensitive silver halide emulsion layer | |
| Monodispersed silver bromochloride emulsion containing 99.5 mol % | 3.0 mg/100 $cm^2$ (in terms of silver) |

-continued

| | |
|---|---|
| or more of AgCl | |
| Cyan coupler (C-1) | 4.2 mg/100 $cm^2$ |
| Tricresyl phosphate | 3.5 mg/100 $cm^2$ |
| Gelatin | 11.5 mg/100 $cm^2$ |
| 6th layer: protective layer | |
| A gelatin layer containing Gelatin | 8.0 mg/100 $cm^2$ |

Next, Samples 28 to 37 of the invention and Comparative Samples 11 to 16 were prepared in the same manner as in Sample 27, except that Example Compound 1 was replaced by an equivalent amount of each of the couplers shown in Table 4.

Each of these samples were subjected to exposure through an optical wedge in an usual manner and then processed according to the following developing procedure and recipes of processing solution.

| Processing step | Temperature | Time |
|---|---|---|
| Color developing | 35.0 ± 0.3° C. | 45 sec |
| Bleach-fixing | 35.0 ± 0.5° C. | 45 sec |
| Stabilizing | 30 to 34° C. | 90 sec |
| Drying | room temperature (25° C.) drying | |

| | |
|---|---|
| [Composition of color developer] | |
| Water | 800 ml |
| Triethanolamine | 10 g |
| N,N'-diethylhydroxylamine | 5 g |
| Potassium bromide | 0.02 g |
| Potassium chloride | 2 g |
| Potassium sulfite | 0.3 g |
| 1-hydroxyethylidene-1,1-diphosphonic acid | 1.0 g |
| EDTA | 1.0 g |
| Disodium catechol-3,5-disulfonate | 1.0 g |
| N-ethyl-N-$\beta$-methanesulfonamidoethyl-3-methyl-4-aminoaniline sulfate | 4.5 g |
| Fluorescent whitening agent (4,4'-diaminostilbene disulfonate) | 10 g |
| Potassium carbonate | 27 g |
| Water was added to make 1 l, then pH was adjusted to 10.10. | |
| [Composition of bleach-fixer] | |
| Ammonium ferric EDTA dihydrate | 60 g |
| EDTA | 3 g |
| Ammonium thiosulfate (70% aqueous solution) | 100 ml |
| Ammonium sulfite (40% aqueous solution) | 27.5 ml |
| Water was added to make 1 l, then pH was adjusted to 6.2 with potassium carbonate or glacial acetic acid. | |
| [Composition of stabilizer] | |
| 5-chloro-2-methyl-4-isothiazoline-3-one | 1.0 g |
| Ethylene glycol | 1.0 g |
| 1-hydroxyethylidene-1,1-diphosphonic acid | 2.0 g |

-continued

| | |
|---|---|
| EDTA | 1.0 g |
| Ammonium hydroxide (20% aqueous solution) | 3.0 g |
| Ammonium sulfite | 3.0 g |
| Fluorescent whitening agent (4,4'-diaminostilbenedisulfonate) | 1.5 g |
| Water was added to make 1 l, then pH was adjusted to 7.0 with sulfuric acid or potassium hydroxide. | |

The maximum dye density and fog of images formed were measured together with the sensitivity of the sample. The results are shown in Table 4. The sensitivity is expressed by a value relative to that of Comparative Sample 11 which is set at 100.

TABLE 4

| Sample No. | Coupler | Fog | Sensitivity | Maximum density |
|---|---|---|---|---|
| 27(Invention) | 1 | 0.03 | 145 | 2.41 |
| 28(Invention) | 4 | 0.02 | 148 | 2.44 |
| 29(Invention) | 13 | 0.03 | 145 | 2.40 |
| 30(Invention) | 15 | 0.03 | 150 | 2.51 |
| 31(Invention) | 23 | 0.02 | 148 | 2.46 |
| 32(Invention) | 25 | 0.03 | 148 | 2.42 |
| 33(Invention) | 28 | 0.03 | 146 | 3.39 |
| 34(Invention) | 47 | 0.04 | 120 | 2.18 |
| 35(Invention) | 50 | 0.03 | 120 | 2.27 |
| 36(Invention) | 60 | 0.05 | 131 | 2.25 |
| 37(Invention) | 65 | 0.03 | 122 | 2.20 |
| 11(Comparison) | Y-5 | 0.06 | 100 | 1.51 |
| 12(Comparison) | Y-6 | 0.07 | 105 | 1.55 |
| 13(Comparison) | Y-7 | 0.04 | 92 | 1.62 |
| 14(Comparison) | Y-8 | 0.07 | 101 | 1.91 |
| 15(Comparison) | Y-9 | 0.06 | 98 | 1.93 |
| 16(Comparison) | Y-10 | 0.06 | 103 | 2.21 |

It is understood from the results shown in Table 4 that the samples of the invention are capable of forming dye images of higher maximum dye density and less fog than the comparative samples, in addition to having a higher sensitivity; thereby it is proved that the couplers of the invention are excellent in color forming property.

As apparent from the results shown in Table 4, the couplers of the invention, unlike the comparative couplers, are capable of providing a sufficient color density even when processed with a developer containing no benzyl alcohol.

EXAMPLE 5

There were sequentially coated on a triacetate film support the following layers having respective compositions to prepared Comparative Sample 17 of a multilayered color photographic light-sensitive material.

| | |
|---|---|
| 1st layer: antihalation layer (HC) | |
| A layer containing black colloidal silver. | |
| 2nd layer: intermediate layer (IL) | |
| A gelatin layer containing a dispersion of 2,5-di-t-octylhydroquinone. | |
| 3rd layer: low speed red-sensitive silver halide emulsion layer (RL) | |
| Monodispersed emulsion containing AgBrI having an average grain size of 0.30 $\mu$m and an AgI content of 6.0 mol % (Emulsion 1) | 1.8 g/$m^2$ (in terms of silver) |
| Sensitizing dye I | $6 \times 10^{-5}$ mol/mol Ag |
| Sensitizing dye II | $1.0 \times 10^{-5}$ mol/mol Ag |
| Cyan coupler (C-2) | 0.06 mol/mol Ag |
| Colored cyan coupler (CC-1) | 0.003 mol/mol Ag |
| DIR compound (D-1) | 0.0015 mol/mol Ag |
| DIR compound (D-2) | 0.002 mol/mol Ag |
| 4th layer: high speed red-sensitive silver halide emulsion layer (RH) | |
| Monodispersed emulsion containing AgBrI having an average grain size of 0.5 $\mu$m and an AgI content of 7.0 | 1.3 g/$m^2$ (in terms of silver) |

-continued

| | |
|---|---|
| mol % (Emulsion II) | |
| Sensitizing dye I | $3 \times 10^{-5}$ mol/mol Ag |
| Sensitizing dye II | $1.0 \times 10^{-5}$ mol/mol Ag |
| Cyan coupler (C-2) | 0.02 mol/mol Ag |
| Colored cyan coupler (CC-1) | 0.0015 mol/mol Ag |
| DIR compound (D-2) | 0.001 mol/mol Ag |
| 5th layer: intermediate layer (IL) | |
| A gelatin layer with the same composition as 2nd layer. | |
| 6th layer: low speed green-sensitive silver halide emulsion layer (GL) | |
| Emulsion I | 1.5 g/m$^2$ (in terms of silver) |
| Sensitizing dye III | $2.5 \times 10^{-5}$ mol/mol Ag |
| Sensitizing dye IV | $1.2 \times 10^{-5}$ mol/mol Ag |
| Magenta coupler (CM-2) | 0.050 mol/mol Ag |
| Colored magenta coupler (CM-1) | 0.009 mol/mol Ag |
| DIR compound (D-1) | 0.0010 mol/mol Ag |
| DIR compound (D-3) | 0.0030 mol/mol Ag |
| 7th layer: high speed green-sensitive silver halide emulsion layer (GH) | |
| Emulsion II | 1.4 g/m$^2$ (in terms of silver) |
| Sensitizing dye III | $1.5 \times 10^{-5}$ mol/mol Ag |
| Sensitizing dye IV | $1.0 \times 10^{-5}$ mol/mol Ag |
| Magenta coupler (M-2) | 0.020 mol/mol Ag |
| Colored magenta coupler (CM-1) | 0.002 mol/mol Ag |
| DIR compound (D-3) | 0.0010 mol/mol Ag |
| 8th layer: yellow filter layer (YC) | |
| A gelatin layer containing a dispersion of yellow colloidal silver and 2,5-di-t-octylhydroquinone. | |
| 9th layer: low speed blue-sensitive silver halide emulsion layer (BL) | |
| Monodispersed emulsion containing AgBrI having an average grain size of 0.48 μm and an AgI content of 6.0 mol % (Emulsion III) | 0.9 g/m$^2$ (in terms of silver) |
| Sensitizing dye V | $1.3 \times 10^{-5}$ mol/mol Ag |
| Comp. yellow coupler (Y-3) | 0.29 mol/mol Ag |
| Tricresyl phosphate | 0.7 ml/m$^2$ |
| 10th layer: high speed blue-sensitive silver halide emulsion layer (BH) | |
| Monodispersed emulsion containing AgBrI having an average grain size of 0.8 μm and an AgI content of 15 mol % (Emulsion IV) | 0.5 g/m$^2$ (in terms of silver) |
| Sensitizing dye V | $1.0 \times 10^{-5}$ mol/mol Ag |
| Comp. yellow coupler (Y-3) | 0.29 mol/mol Ag |
| DIR compound (D-2) | 0.0015 mol/mol Ag |
| Tricresyl phosphate | 0.2 ml/m$^2$ |
| 11th layer: 1st protective layer (Pro-1) | |
| A gelatin layer containing silver iodobromide (AgI: 1 mol %, average grain size: 0.07 μm, coating weight in terms of silver: 0.5 g/m$^2$) and UV absorbents UV-3 and UV-4 (1:1). | |
| 12th layer: 2nd protective layer (Pro-2) | |
| A gelatin layer containing polymethylmethacrylate powder (average particle size: 1.5 μm) and formalin scavenger (HS-1). | |

In addition to the above component, a gelatin hardener (H-1) and a surfactant were added to each layer.

Further, samples shown in Table 5 were prepared in the same manner as in Comparative Sample 17, except that the Comparative coupler Y-3 used in the 9th and 10th layers of Comparative Sample 17 was replaced by couplers shown in Table 5.

Components used in above samples are as follows:

Sensitizing dye I:
Anhydro-5,5'-dichloro-9-ethyl-3,3'-di-(3-sulfopropyl) thiacarbocyaninehydroxide -continued Sensitizing dye II:
Anhydro-9-ethyl-3,3'-di-(3-sulfopropyl)-4,5,4',5'-dibenzothiacarbocyaninehydroxide
Sensitizing dye III:
Anhydro-5,5'-diphenyl-9-ethyl-3,3'-di-(3-sulfopropyl) oxacarbocyaninehydroxide
Sensitizing dye IV:
Anhydro-9-ethyl-3,3'-di-(3-sulfopropyl)-5,6,5',6'-dibenzoxacarbocyaninehydroxide
Sensitizing dye V:
Anhydro-3,3'-di-(3-sulfopropyl)-4,5-benzo-5'-methoxythiacyaninehydroxide

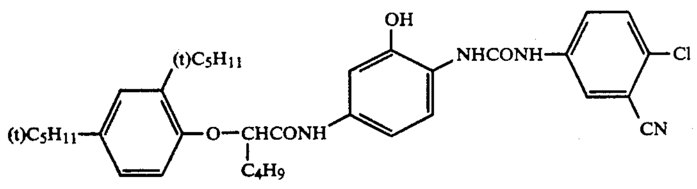
C-2
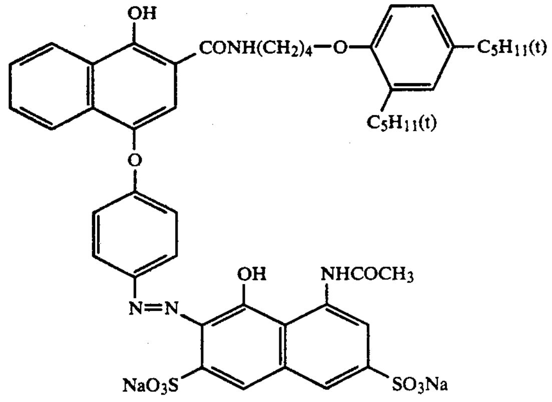
CC-1
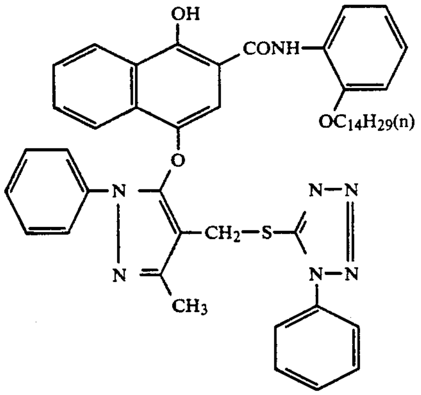
D-1
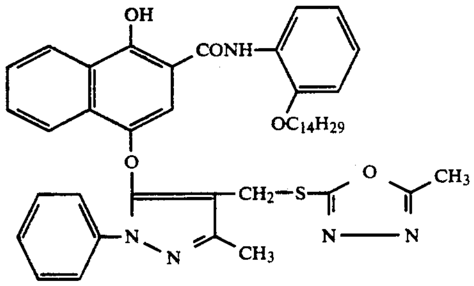
D-2

-continued
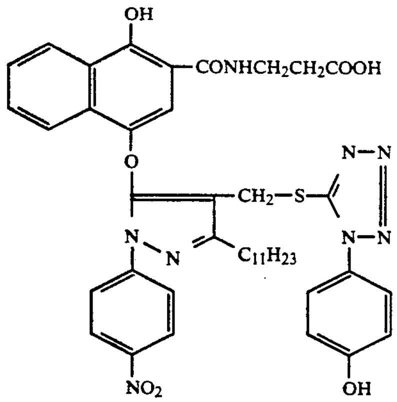
D-3
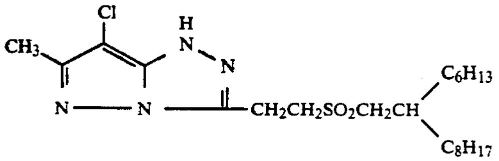
M-2
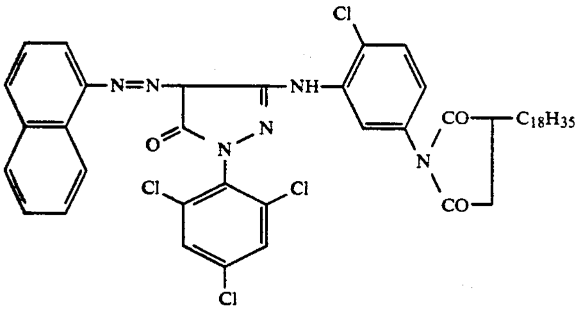
CM-1
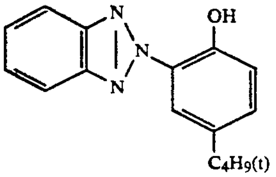
UV-3
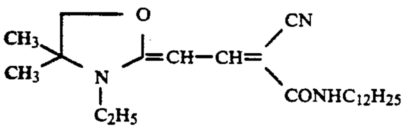
UV-4
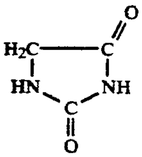
HS-1
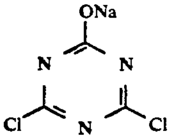
H-1

-continued

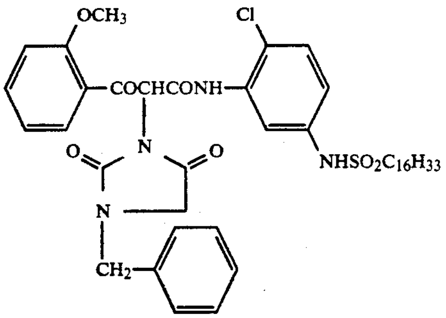

Y-6

The samples prepared as above were exposed through an optical wedge and processed according to the following developing procedure and recipes of processing solution.

| Processing step (at 38° C.) | Time |
|---|---|
| Color developing | |
| Bleaching | 3 min 15 sec |
| Washing | 6 min 30 sec |
| Fixing | 3 min 15 sec |
| Washing | 6 min 30 sec |
| Stabilizing | 3 min 15 sec |
| Drying | 1 min 30 sec |
| Composition of each processing solution is as follows: | |
| [Color developer] | |
| 4-amino-3-methyl-N-ethyl-N-(β-hydroxyethyl)aniline sulfate | 4.75 g |
| Anhydrous sodium sulfite | 4.25 g |
| Hydroxylamine ½ sulfate | 2.0 g |
| Anhydrous potassium carbonate | 37.5 g |
| Sodium bromide | 1.3 g |
| Trisodium nitrilotriacetate monohydrate | 2.5 g |
| Potassium hydroxide | 1.0 g |
| Water was added to make 1 l. | |
| [Bleacher] | |
| Ammonium ferric EDTA | 100.0 g |
| Diammonium EDTA | 10.0 g |
| Ammonium bromide | 150.0 g |
| Glacial acetic acid | 10.0 ml |
| Water was added to make 1 l, then pH was adjusted to 6.0 with aqueous ammonia. | |
| [Fixer] | |
| Ammonium thiosulfate | 175.0 g |
| Anhydrous sodium sulfite | 8.5 g |
| Sodium metasulfite | 2.3 g |
| Water was added to make 1 l, then pH was adjusted to 6.0 with acetic acid. | |
| [Stabilizer] | |
| Formalin | 1.5 ml |
| Koniducks (made by Konica Corp.) | 7.5 ml |
| Water was added to make 1 l. | |

The evaluation results are shown in Table 5.

TABLE 5

| Sample No. | Coupler No. | ΔFog*1 | Maximum density | Relative sensitivity |
|---|---|---|---|---|
| 17 (Comparison) | Y-3 | +0.04 | 2.18 | 92 |
| 18 (Comparison) | Y-6 | +0.05 | 2.24 | 94 |
| 38 (Invention) | 7 | ±0 | 2.38 | 100 |

TABLE 5-continued

| Sample No. | Coupler No. | ΔFog*1 | Maximum density | Relative sensitivity |
|---|---|---|---|---|
| 39 (Invention) | 33 | ±0 | 2.43 | 105 |
| 40 (Invention) | 34 | ±0 | 2.36 | 98 |
| 41 (Invention) | 35 | +0.01 | 2.46 | 108 |
| 42 (Invention) | 36 | +0.02 | 2.44 | 106 |
| 43 (Invention) | 37 | +0.01 | 2.52 | 111 |
| 44 (Invention) | 38 | +0.01 | 2.43 | 106 |
| 45 (Invention) | 39 | ±0 | 2.44 | 108 |
| 46 (Invention) | 40 | +0.01 | 2.49 | 110 |
| 47 (Invention) | 41 | +0.02 | 2.41 | 99 |
| 48 (Invention) | 42 | +0.01 | 2.39 | 101 |
| 49 (Invention) | 43 | ±0 | 2.38 | 98 |

*1Difference in fog from Sample 38
*2Relative sensitivity when the sensitivity of Sample 38 is set at 100.

It can be found from Table 5 that the couplers of the invention can raise the density and sensitivity without facilitating occurrence of fog as compared with the comparative couplers.

EXAMPLE 6

Comparative Sample 19(A) of a multilayered color photographic material was prepared by forming layers of the same configuration and composition as Comparative Sample 17 of Example 5 on a triacetyl cellulose film support, except that Y-1 was used as a comparative coupler instead of Y-3.

Comparative Sample 19 (B) of a multilayered color photographic material was prepared in the same manner as in Comparative Sample 19 (A), except that a coupler dispersion maintained at 40° C. for 8 hours after the preparation was used instead of a freshly prepared coupler dispersion used in Comparative Sample 19 (A).

Further, comparative samples and samples of the invention were prepared in the same way as the above, except that the couplers shown in Table 6 were used instead of Comparative coupler Y-1 used in the 9th and 10th layers of Comparative Samples 19 (A) and (B).

Each sample prepared as above was subjected to exposure through an optical wedge in a normal manner, followed by processing according to the developing procedure and recipes of processing solution in Example 5.

The image formed on each sample was evaluated for the maximum dye density, as well as the measurement of sensitivity on each sample. The results are shown in Table 6.

TABLE 6

| Sample No. | | Coupler | | Samples using fresh coupler Dispersion (A) Sensitivity | Maximum density | Samples using stored coupler Dispersion (B) Sensitivity | Maximum density |
|---|---|---|---|---|---|---|---|
| Sample of the | 50 | Example | 71 | 109 | 2.28 | 105 | 2.22 |
| invention | 51 | Coupler | 72 | 110 | 2.32 | 104 | 2.24 |
| | 53 | | 75 | 111 | 2.30 | 105 | 2.25 |
| Comparative | 19 | Comparative | Y-1 | 100 | 2.12 | 85 | 1.72 |
| Sample | 20 | coupler | Y-2 | 105 | 2.19 | 89 | 1.81 |
| | 21 | | Y-4 | 94 | 1.82 | 72 | 1.58 |

*The sensitivity is expressed by a value relative to that of Comparative Sample 19 (A) which is set at 100.

It is understood from the results shown in Table 6 that in both Samples (A) and (B), the samples of the invention can provide maximum dye densities higher than those of the comparative samples and cause less deterioration in sensitivity and maximum dye density between Samples (A) an d(B) than the comparative samples. This proves that the couplers of the invention are excellent in dispersion stability immediately after the preparation of couplers dispersion and even after the standing of coupler dispersion.

EXAMPLE 7

On a subbed triacetyl cellulose film support were formed the following layers in order to prepared Comparative Sample 22 of multilayered color photographic material. The coating weight of each component is in $g/m^2$.

| | |
|---|---|
| 1st layer: antihalation layer | |
| UV absorbent (UV-3) | 0.3 |
| UV absorbent (UV-4) | 0.4 |
| High boiling solvent (Oil-1) | 1.0 |
| Black colloidal silver | 0.24 |
| Gelatin | 2.0 |
| 2nd layer: intermediate layer | |
| 2,5-di-t-octylhydroquinone | 0.1 |
| High boiling solvent (Oil-1) | 0.2 |
| Gelatin | 1.0 |
| 3rd layer: low speed red-sensitive silver halide emulsion layer | |
| Silver iodobromide emulsion spectrally sensitized by red sensitizing dyes S-1 and S-2 (AgI: 4.0 mol %, average grain size: 0.25 μm) | 0.5 |
| Coupler (C-1) | 0.1 mol |
| High boiling solvent (Oil-2) | 0.6 |
| Gelatin | 1.3 |
| 4th layer: high speed red-sensitive silver halide emulsion layer | |
| Silver iodobromide emulsion spectrally sensitized by red sensitizing dyes S-1 and S-2 (AgI: 2.0 mol %, average grain size: 0.6 μm) | 0.8 |
| Coupler (C-1) | 0.2 mol |
| High boiling solvent (Oil-2) | 1.2 |
| Gelatin | 1.8 |
| 5th layer: intermediate layer | |
| 2,5-di-t-octylhydroquinone | 0.1 |
| High boiling solvent (Oil-1) | 0.2 |
| Gelatin | 0.9 |
| 6th layer: low speed green-sensitive silver halide emulsion layer | |
| Silver iodobromide emulsion spectrally sensitized by green sensitizing dyes S-3 and S-4 (AgI: 4.0 mol %, average grain size: 0.25 μm) | 0.6 |

-continued

| | |
|---|---|
| Coupler (C-2) | 0.04 mol |
| Coupler (C-3) | 0.01 mol |
| High boiling solvent (Oil-3) | 0.5 |
| Gelatin | 1.4 |
| 7th layer: high speed green-sensitive silver halide emulsion layer | |
| Silver iodobromide emulsion spectrally sensitized by green sensitizing dyes S-3 and S-4 (AgI: 2.0 mol %, average grain size: 0.6 μm) | 0.9 |
| Coupler (C-2) | 0.10 mol |
| Coupler (C-3) | 0.02 mol |
| High boiling solvent (Oil-3) | 1.0 |
| Gelatin | 1.5 |
| 8th layer: intermediate layer | |
| The same as 5th layer. | |
| 9th layer: yellow filter layer | |
| Yellow colloidal silver | 0.1 |
| Gelatin | 0.9 |
| 2,5-di-t-octylhydroquinone | 0.1 |
| Hydroquinone | 0.1 |
| High boiling solvent (Oil-1) | 0.2 |
| 10th layer: low speed blue-sensitive silver halide emulsion layer | |
| Silver iodobromide emulsion spectrally sensitized by blue sensitizing dyes S-5 (AgI: 4.0 mol %, average grain size: 0.35 μm) | 0.6 |
| Comparative coupler (Y-7) | 0.3 mol |
| High boiling solvent (Oil-3) | 0.6 |
| Gelatin | 1.3 |
| 11th layer: high speed blue-sensitive silver halide emulsion layer | |
| Silver iodobromide emulsion spectrally sensitized by blue sensitizing dyes S-5 (AgI: 2.0 mol %, average grain size: 0.9 μm) | 0.9 |
| Comparative coupler (Y-7) | 0.5 mol |
| High boiling solvent (Oil-3) | 1.4 |
| Gelatin | 2.1 |
| 12th layer: 1st protective layer | |
| UV absorbent (UV-3) | 0.3 |
| UV absorbent (UV-4) | 0.4 |
| High boiling solvent (Oil-3) | 0.6 |
| Gelatin | 1.2 |
| 2,5-di-t-octylhydroquinone | 0.1 |
| 13th layer: 2nd protective layer | |
| Emulsion of nonlight-sensitive silver halide grains containing silver iodobromide having a silver iodide content of 1 mol % and an average grain size (r̄) of 0.08 μm. | 0.3 (in terms of silver) |
| Polymethylmethacrylate powder (dia.: 1.5 μm) | 0.05 |
| Surfactant (Su-1) | 0.005 |
| Gelatin | 0.7 |

In addition to the above compounds, a gelatin hardener (H-1) and a surfactant were added to each of the foregoing layers. As a solvent for couplers, tricresyl phosphate was used.

Sensitizing dye S-1

-continued
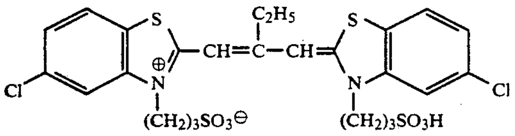
Sensitizing dye S-2
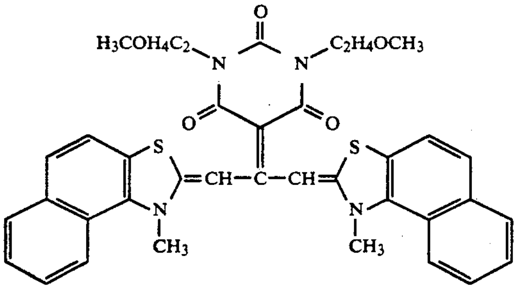
Sensitizing dye S-3
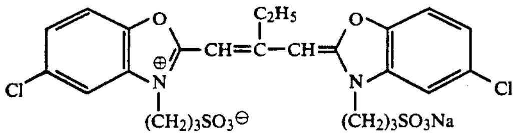
Sensitizing dye S-4
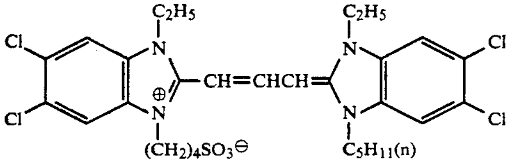
Sensitizing dye S-5
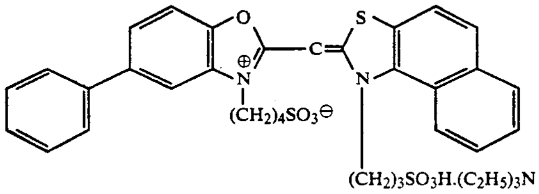
Oil-1
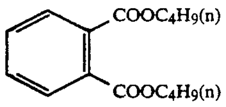
Oil-2
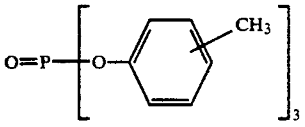
Oil-3
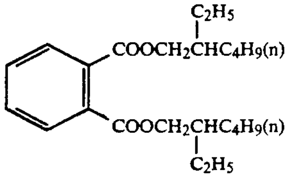
Coupler C-1

-continued

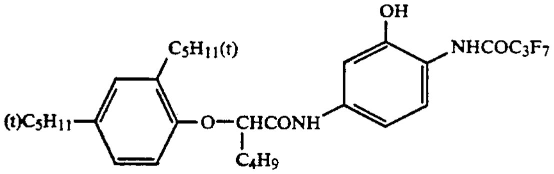

Coupler C-2

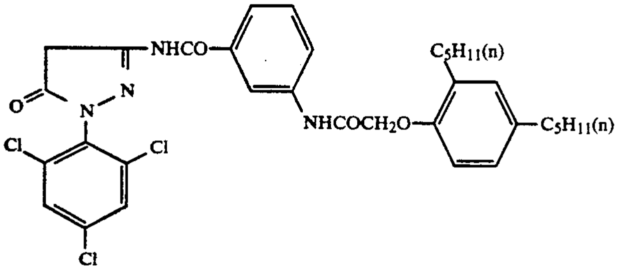

Coupler C-3

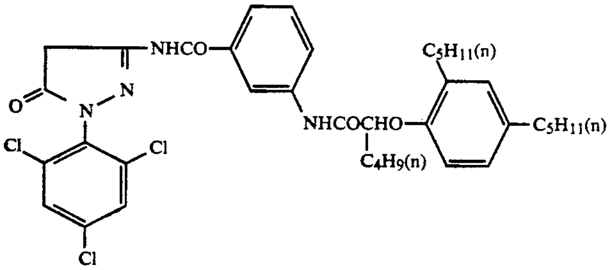

Surfactant-1

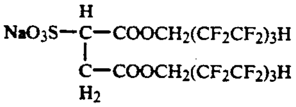

Further, multilayered color photographic material samples were prepared in the same manner as in Comparative Sample 22, except that the yellow couplers used in the 10th and 11th layers were varied as shown in Table 7.

The samples were exposed through an optical wedge and then processed according to the following developing procedure and recipes of processing solution.

| Reversal processing step | Time | Temperature |
|---|---|---|
| 1st developing | | |
| Washing | 6 min | 38° C. |
| Reversing | 2 min | 38° C. |
| Color developing | 2 min | 38° C. |
| Conditioning | 6 min | 38° C. |
| Bleaching | 2 min | 38° C. |
| Fixing | 6 min | 38° C. |
| Washing | 4 min | 38° C. |
| Stabilizing | 4 min | 38° C. |
| Drying | 1 min | room temp. |

Composition of each processing solution was as follows:

| | |
|---|---|
| [1st developer] | |
| Sodium tetrapolyphosphate | 2 g |
| Sodium sulfite | 20 g |
| Hydroquinone monosulfonate | 30 g |
| Sodium carbonate monohydrate | 30 g |
| 1-phenyl-4-methyl-4-hydroxymethyl-3-pyrazolidone | 2 g |
| Potassium bromide | 2.5 g |
| potassium thiocyanate | 1.2 g |

-continued

| | |
|---|---|
| Potassium iodide (0.1% solution) | 2 ml |
| Water to make | 1000 ml |
| [Reversing solution] | |
| Hexasodium nitrilotrimethylene phophonate | 3 g |
| Stannous chloride dihydrate | 1 g |
| p-aminophenol | 0.1 g |
| Sodium hydroxide | 8 g |
| Glacial acetic acid | 15 ml |
| Water to make | 1000 ml |
| [Color developer] | |
| Sodium tetrapolyphosphate | 3 g |
| Sodium sulfite | 7 g |
| Sodium orthophosphate (12 hydrate) | 36 g |
| Potassium bromide | 1 g |
| Potassium iodide (0.1% solution) | 90 ml |
| Sodium hydroxide | 3 g |
| Citrazinic acid | 1.5 g |
| N-ethyl-N-β-methanesulfonamidoethyl-3-methyl-4-aminoaniline sulfate | 11 g |
| 3,2-ethylenedithioethanol | 1 g |
| Water to make | 1000 ml |
| [Conditioner] | |
| Sodium sulfite | 12 g |
| Sodium EDTA (dihydrate) | 8 g |
| Thioglycerin | 0.4 ml |
| Glacial acetic acid | 3 ml |
| Water to make | 1000 ml |
| [bleacher] | |
| Sodium EDTA (dihydrate) | 2.0 g |
| Ammonium ferric EDTA (dihydrate) | 120.0 g |
| Ammonium bromide | 100.0 g |
| Water to make | 1000 ml |

-continued

| | | |
|---|---|---|
| [Fixer] | | |
| Ammonium thiosulfate | 80.0 | g |
| Sodium sulfite | 5.0 | g |
| Sodium bisulfite | 5.0 | g |
| Water to make | 1000 | ml |
| [Stabilizer] | | |
| Formalin (37 wt % solution) | 5.0 | ml |
| Koniducks (made by Konica Corp.) | 5.0 | ml |
| Water to make | 1000 | ml |

The samples processed with the above processing solutions were evaluated for the maximum density (D max) with blue light. The results are shown in Table 7.

TABLE 7

| Sample No. | Coupler No. | ΔFog*1 | Maximum density |
|---|---|---|---|
| 22 (Comparison) | Y-1 | +0.03 | 2.98 |
| 23 (Comparison) | Y-2 | +0.02 | 2.92 |
| 24 (Comparison) | Y-3 | +0.06 | 3.03 |
| 25 (Comparison) | Y-4 | +0.05 | 3.01 |
| 26 (Comparison) | Y-6 | +0.06 | 3.1 |
| 54 (Invention) | 2 | ±0 | 3.28 |
| 55 (Invention) | 3 | +0.02 | 3.31 |
| 56 (Invention) | 4 | +0.01 | 3.32 |
| 57 (Invention) | 12 | +0.01 | 3.30 |
| 58 (Invention) | 23 | +0.01 | 3.29 |
| 59 (Invention) | 24 | +0.02 | 3.27 |
| 60 (Invention) | 26 | +0.02 | 3.35 |
| 61 (Invention) | 27 | +0.01 | 3.30 |
| 62 (Invention) | 33 | +0.02 | 3.39 |

*1Difference in fog from Sample 45

As shown in Table 7, the yellow couplers of the invention can provide a good dye density without causing a rise in fogging.

What is claimed is:

1. A silver halide photographic light-sensitive material comprising a support having thereon a silver halide emulsion layer, wherein at least one of said emulsion layers contains a coupler represented by the following Formula (I), (II) or (III):

Formula (I)

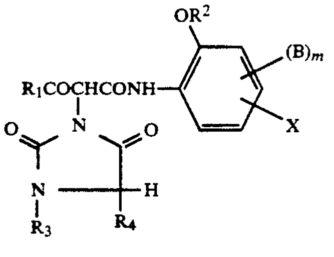

Wherein $R_1$ and $R_2$ independently represent an alkyl group, cycloalkyl group or aryl group; $R_3$ and $R_4$ independently represent an alkyl group or cycloalkyl group; B represents a substituent; m represents an integer of from 0 to 3; and X represents an acylamino group, sulfonamide group, oxycarbonyl group, carbamoyl group, sulfamoyl group, carbonyloxy group, oxycarbonylamino group, ureido group or sulfonyloxy group;

Formula (II)

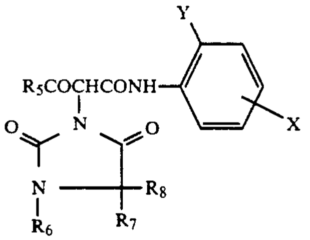

wherein $R_5$ represents wherein an alkyl group or cycloalkyl group; $R_6$ and $R_7$ independently represent an alkyl group or cycloalkyl group, and $R_8$ represents a hydrogen atom, alkyl group or cycloalkyl group, provided that the total carbon number of $R_6$, $R_7$ and $R_8$ is 7 or less; X is the same as defined in Formula (I); and Y represents a halogen atom, amino group, alkylthio group or arylthio group;

Formula (III)

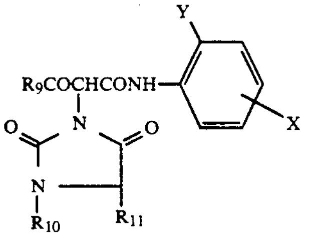

Wherein $R_9$ represents an aryl group; $R_{10}$ and $R_{11}$ independently represent an alkyl group or cycloalkyl group, provided that the total carbon number of $R_{10}$ and $R_{11}$ is 9 or less; X and Y are the same as defined in Formula (I) and (II).

2. A silver halide photograhic light-sensitive material of claim 1, wherein said $R_1$ of Formula (I) represents a branched alkyl group.

3. A silver halide photographic light-sensitive material of claim 2, wherein said $R_1$ is t-butyl.

4. A silver halide photographic light-sensitive material of claim 1, wherein said $R_2$ of Formula (I) represents a linear or branched alkyl group.

5. A silver halide photographic light-sensitive material of claim 1, wherein said $R_5$ of Formula (II) represents a branched alkyl group.

6. A silver halide photographic light-sensitive material of claim 1, wherein said Y of Formula (II) represents a halogen atom.

7. A silver halide photographic light-sensitive material of claim 6, wherein said Y is a chlorine atom.

8. A silver halide photographic light-sensitive material of claim 1, wherein said $R_9$ of Formula (III) is a methoxy-phenyl group.

9. A silver halide photographic light-sensitive material of claim 1, wherein said X of Formula (I), (II) and (III) is a group selected from the groups represented by following formulas (1) to (11):

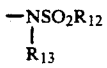

formula (1)

$-CONR_{12}R_{13}$ formula (2)

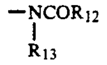

formula (3)

-continued

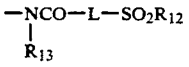

formula (4)

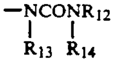

formula (5)

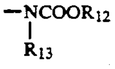

formula (6)

$-OSO_2R_{12}$ formula (7)

$-OCOR_{12}$ formula (8)

$-COOR_{12}$ formula (9)

-continued $-COO-L-COOR_{12}$ formula (10)

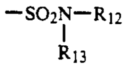

formula (11)

wherein $R_{12}$ represents an alkyl group, cycloalkyl group or aryl group; $R_{13}$ and $R_{14}$ independently represent a hydrogen atom or a group represented by $R_{12}$; and L represents a divalent organic linking group.

10. A silver halide photographic light-sensitive material of claim 1, wherein an amount of said coupler represented by Formula (I), (II) or (III) contained in said silver halide emulsion layer is within the range of from 10 to 300 g per mol of silver halide contained in said emulsion layer.

* * * * *